(12) United States Patent
Xu et al.

(10) Patent No.: US 8,859,744 B2
(45) Date of Patent: Oct. 14, 2014

(54) RECOMBINANT HYDROGEN-PRODUCING CYANOBACTERIUM AND USES THEREOF

(75) Inventors: Qing Xu, North Potomac, MD (US); Hamilton O. Smith, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 1050 days.

(21) Appl. No.: 12/445,929

(22) PCT Filed: Oct. 16, 2007

(86) PCT No.: PCT/US2007/022099
§ 371 (c)(1),
(2), (4) Date: Aug. 3, 2010

(87) PCT Pub. No.: WO2008/143630
PCT Pub. Date: Nov. 27, 2008

(65) Prior Publication Data
US 2010/0291651 A1    Nov. 18, 2010

Related U.S. Application Data

(60) Provisional application No. 60/851,758, filed on Oct. 16, 2006.

(51) Int. Cl.
C07H 21/02 (2006.01)
C12N 7/00 (2006.01)
C12P 3/00 (2006.01)
C12N 13/00 (2006.01)
C12N 9/02 (2006.01)

(52) U.S. Cl.
CPC . *C12P 3/00* (2013.01); *C12N 13/00* (2013.01); *C12N 9/0067* (2013.01)

USPC .................................. 536/23.1; 435/235.1

(58) Field of Classification Search
None
See application file for complete search history.

(56) References Cited

U.S. PATENT DOCUMENTS

2002/0164706 A1* 11/2002 Huang et al. ............... 435/69.1

OTHER PUBLICATIONS

Lodders et al., Frequent genetic recombination in natural populations of the marine cyanobacterium *Microcoleus* chthonoplastes., Environmental Microbiology, (Mar. 2005) vol. 7, Issue 3, pp. 434-442; Title and Abstract only.*
Lopez-Lopez et al., Genetic analysis of housekeeping genes reveals a deep-sea ecotype of *Alteromonas macleodii* in the Mediterranean Sea., Environmental Microbiology, (Epub Jan. 28, 2005), vol. 7, Issue 5, pp. 649-659.*
Weyman et al., Heterologous expression of *Alteromonas macleodii* and *Thiocapsa roseopersicina* [NiFe] hydrogenases in *Synechococcus elongatus.*, PLoS One. 2011, vol. 6(5), e20126, pp. 1-8.*
Vargas et al., [NiFe] hydrogenase from *Alteromonas macleodii* with unusual stability in the presence of oxygen and high temperature., Appl Environ Microbiol. (Mar. 2011;77) vol. 6, pp. 1990-1998.*
Ivars-Martinez et al., Comparative genomics of two ecotypes of the marine planktonic copiotroph *Alteromonas macleodii* suggests alternative lifestyles associated with different kinds of particulate organic matter., The ISME Journal, (E pub Jul. 21, 2008) vol. 2, pp. 1194-1212.*

(Continued)

*Primary Examiner* — Alexander Kim
(74) *Attorney, Agent, or Firm* — DLA Piper LLP (US)

(57) ABSTRACT

A recombinant cyanobacterium comprising an oxygen-tolerant, hydrogen-evolving hydrogenase, kit, and methods of use.

12 Claims, 17 Drawing Sheets

(56) References Cited

OTHER PUBLICATIONS

Asada et al., Production of Bioplastics and Hydrogen Gas by Photosynthetic Microorganisms., Chin. J. Oceanol. Limnol. (1998), vol. 16 Suppl., pp. 91-104.*

Guo et al., Protein tolerance to random amino acid change, 2004, Proc. Natl. Acad. Sci. USA 101: 9205-9210.*

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Burke et al., Oxygen Tolerance of the H2-sensing [NiFe] Hydrogenase from *Ralstonia eutropha* H16 is Based on Limited Access of Oxygen to the Active Site., The Journal of Biological Chemistry (Apr. 22, 2005), vol. 280, pp. 23791-23796.*

Fodor et al., Modular Broad-Host-Range Expression Vectors for Single-Protein and Protein Complex Purification., Applied and Environmental Microbiology (2004), vol. 70, pp. 712-721.*

Ghirardi et al., Proceedings of the 2001 DOE Hydrogen Program Review, published on 2001, pp. 1-10.*

Branden and Tooze, Intorduction to Protein Structure (1999), 2nd edition, Garland Science Publisher, pp. 3-12.*

Unger et al., The Genetic Algorithm approach to Protein Structure Prediction, Structure and Bonding (2004), vo. 110, pp. 153-175.*

Bhanothu et al., Review on characteristic developments of computational protein engineering, Journal of Pharmaceutical Research and Opinion (2012), vol. 2:8, pp. 70-93.*

Grunberg et al., Strategies for protein synthetic biology, Nucleic Acids Research (2010), vol. 38(8), pp. 2663-2675.*

Li et al.-B (Current Approaches for Engineering Proteins with Diverse Biological Properties, Adv Exp Med Biol. (2007-B) vol. 620, pp. 18-33.*

Someya et al. Proceeding GECCO '09 Proceedings of the 11th Annual conference on Genetic and evolutionary computation, pp. 233-240 ACM New York, NY, USA © 2009.*

Goomber et al., Enhancing thermostability of the biocatalysts beyond their natural function via protein engineering, International Journal for Biotechnology and Molecular Biology Research, (2012), vol. 3(3), pp. 24-29.*

Buske et al., In silico characterization of protein chimeras: Relating sequence and function within the same fold, Proteins (2009), vol. 77, Issue 1, pp. 111-120.*

Qu et al., A Guide t Template Based Structure Prediction., Current Protein and Peptide Science (2009), vol. 10, pp. 270-285.*

Das and Veziroğu, "Hydrogen production by biological processes: a survey of literature", International Journal of Hydrogen Energy, 26(1):13-28 (2001).

Database UniProt [Online], Jun. 1, 1998, "SubName: Full=Stable NiFe hydrogenase small subunit; Flags: Precursor", retrieved from EBI accession No. UNIPROT:O51820 (XP002506022).

Database UniProt [Online], Jun. 1, 1998, "SubName: Full=Stable NiFe hydrogenase large subunit", retrieved from EBI accession No. UNIPROT:O51823 (XP002506023).

Database UniProt [Online], Sep. 23, 2008, "SubName: Full=Ni—Fe hydrogenase, small subunit", retrieved from EBI accession No. UNIPROT:B4S321 (XP002506024).

Database UniProt [Online], Sep. 23, 2008, "SubName: Full=Ni—Fe hydrogenase large chain", retrieved from EBI accession No. UNIPROT:B4S322 (XP002506025).

Ghirardi et al., "Approaches to developing biological H(2)-photoproducing organisms and processes", *Biochem. Soc. Trans.*, 33(Pt 1):70-72 (2005).

Gogotov I.N., "Hydrogenases of phototrophic microorganisms", *Biochimie*, 68(1):181-187 (1986).

Hansel and Lindblad, "Towards optimization of cyanobacteria as biotechnologically relevant producers of molecular hydrogen, a clean and renewable energy source", *Applied Microbiology and Biotechnology*, 50(2):153-160 (1998).

Maness et al, "Characterization of the oxygen tolerance of a hydrogenase linked to a carbon monoxide oxidation pathway in *Rubrivivax gelatinosus*", *Appl. Environ. Microbiol.*, 68(6):2633-2636 (2002).

Rakhely et al., "Unusual organization of the genes coding for HydSL, the stable [NiFe]hydrogenase in the photosynthetic bacterium *Thiocapsa roseopersicina* BBS", *Journal of Bacteriology*, 180(6):1460-1465 (1998).

Schnackenberg et al., "In vitro and in vivo coupling of *Thiocapsa* hydrogenase with cyanobacterial and algal electron mediators", *J. Biosci. Bioeng.*, 88(1):30-34 (1999).

Venter et al., "Environmental genome shotgun sequencing of the Sargasso Sea", *Science*, 304(5667):66-74 (2004).

Zadvorny et al., "Properties of stable hydrogenase from the purple sulfur bacterium *Lamprobacter modestohalophilus*", *Biochemistry* (Moscow)., 69(2):164-169 (2004).

International Search Report (ISR) from PCT/US2007/022099. (mailed Dec. 2008).

* cited by examiner

Figure 4

```
AmDE   MKRLRRIEMALPTLNKQLQASGISRRTFLKFCATTASLLALPQSAVADLATATALGNARRPS  60
HynS   ---MAARNPTDKTLGESLRERGVSRRGFLKFCAATASMMALPPSMAPAIAAALEQAKRPS    57
          : :*  ***:.*:  **.:.****.****.*******:*.*:****

AmDE   VIWLPFQECTGCTEAILRSHAPTLESLIFDHISLDYQHTIMAAAGEQAEDARRAAMNAHK   120
HynS   VIWLSFQECTGCTESLTRSHAPTLEDLILDVISLDYHHTLQAAAGDAAEHAREQAMAANP   117
       **** *********:::********:** * *****::*:: ** *. ** *:. * *

AmDE   GQYLLLVDGSVP-VGNPGYSTISGMSNVDMLRESAKDAAGIIAIGTCASFGGIPKANPN   178
HynS   GEYLVIVDGSIPGPDSNPGYSTVAGHSNYAMLMETVENAAAVIAVGTCATFGGLPGANPN   177
       *:**::****:*   .:*****::*:**  ** . :: ****:**:****:***:* ***

AmDE   PTGAVAVSDIITDKPIVNISGCPPLPIAITAVLVHYLTFKRFPDLDELQRPLAFFGESIH   238
HynS   PTGAMSVMDLVKDKPVINVSGCPPIPMVITGVIAHYLTFGRLPELDAYNRPMAFFGQSIH   237
       ****.:* *:::***::*:*****:*:.:**.*:.***** *:*:*  :**:****:***

AmDE   DRCYRRPFFEQRKFAKSFDDEGAKNGWCLFELGCKGPETFNACATVKWNQGTSFPIESGH   298
HynS   DRCYRRPFYDKGLFAKTFDDEGARLGWCLYELGCKGPTTYNACATMRWNDGTSWPVEAGH   297
       ********::: :***:******: ****:******: :******::**:*** *:*:**

AmDE   -----------GPWEWYKSKPGKGAQKHA    336
HynS   PCLGCSEPRFWDAGGFYNTVSVPTSASGVNVLAAGAAGAIVGGAVAALAKKQTKTAVAHR   357
                   *  .  *     *   . *    :*

AmDE   GKNS------ 340
HynS   QPVTVEELEAKL 369
```

Figure 5

```
AmDE    MENTASNNRLVVDPITRIEGHLRIEAEMDGNTIKQAFSSGTSVRGIELILQGRDPRDAWA    60
HynL    ----MSERIVVDPVTRIEGHLRIEAQMDGENIAQAYSSGTSVRGLETILKGRDPRDAWA    55
        .:*:*************:****:****:**   *:**:********* ***.********

AmDE    FAQRICGVCTLVHGMASVRAVEDAIRKAWRSNAKLGVAIGKPSMTSMPKGPMQHGKKGHR   120
HynL    FAQRICGVCTLVHGIASVRSVEDALK----------------------------------    81
        **************:****:****:*

AmDE    QSRTSIGVLSEAEMAIPQNAQVIRNIMIATQYVHDHVMHFYHLHALDWVVSALDADPT    180
HynL    ----------IELPPNAQLIRNLMISSQFVHDHVMHFYHLHALDWVVSALSADPK.   128
                  : :* ****:***:**::**:**************************.***.

AmDE    RTATLAGQLSDYPRSSPGYFKDVKQKVKTLVESGQLGIFSNAYWGHPGYKLPPEVNLMAL   240
HynL    ATSDLAQSISSWPKSSPGYFADTQKRIKTFVESGQLGIFANGYWGHPAYKLPPEANLMAV   188
        *:** ..*:*.:***.*****.* :::**:**:*******:* .******.******.****:

AmDE    AHYLDALTWQREVVKVHTIFGGKNPHPNFVVGGVPSPINLNASTGINTSRLVQLQDAITQ   300
HynL    AHYLEALAWQRDVARLHAIFGGKNPHPNFVVGGVPSPIDIDSDSAINAKRLAEVQQILQS   248
        ****:**:***:*.::*:**********************:::.:. ***.:**:  **.  ..
```

Figure 5 (continued)

```
AmDE    MKSFVDQVYPDIVAIAGYYKEWGTRGEGLGNFLTYGDLPMTSMDDPDSFLFPRGAILGR  360
HynL    MQTFVDQVYVPDTLAIASFYKDWGERGEGLGNFMSYGDLPATGTMDPAQFLFPRGVILNR  308
        *:*.******  **  :****.:.:****.:.*******::;******  *.  **  .*********.*.*

AmDE    DLSKVHDLDLDDPSEIQEFVSSSWYRYSGGNASGLHPFNGQTTLEYTGP--KPPYKHLN  417
HynL    DLSTIHEIDLHDAGQIQEYVAHSWYEYSGGNDQGLHPYDGETNLEYDARGGVKPPYTQLD  368
        ***.:*::**.*:.:****:**.:**: *****:  ****::**  ****  ****::**  .

AmDE    VGAEYSWLKSPRWKGHAMEVGPLARVLMMYAKKDAAAQDIVNRSLSILDLETSALFSTLG  477
HynL    VNDGYSWMKAPRWKGHAMEVGPLARVLLLYASGHEQTKELVEMTLTTLDLPVRALYSTLG  428
        *.  ****:*:**********:**.    .::::*:  ***  .    **  .*****

AmDE    RTLARAVETKIVVNQLSWYDQLLDNIAKGDTDTFNPLYFDPTNWPIKGQGVGVMEAPRG  537
HynL    RTAARTLETKILTDTAQDWYNQLIANIKAGDSRTFNETLWEPSSWPAEARGAGYMEAPRG  488
        **  **: :***:. :*  .****:.****:.:*** *..:.*. * ********

AmDE    ALGHWLVMQNGKIENYQCVVPTTWNAGPRDPNSQAGAYEAALQDKHTLHDPDQPLEILRT  597
HynL    ALGHWIVIKDRKIANYQAVVPSTWNAGPRDPSDQPGAYEAALQDNHQLVDVKQPIEILRT  548
        *****:*::: :** ****.******** .*.**********:*  *  *  :**:****

AmDE    LHSFDPCLACAVHVMDETGEERLRLKVR  625
HynL    IHSFDPCIACAVHLTDPETGEQMEIKIT  576
        :******:*****: * ****:  *:::*:
```

1: *T. roseopersicina* wild-type strain (BBS), positive control
2: *T. roseopersicina* GB112131 strain containing pAMDHSL (AmDHSL)
3: *T. roseopersicina* ΔHyn, ΔHup, ΔHox strain (GB112131), negative control
M: Bio-Rad Protein Ladders Primary antibody raised against *T. roseopersicina* Hyn was used for Western blotting High O₂ / thermal stability, and resistance to proteolysis
➤ Structural subunit: HynS and HynL
➤ Electron transfer subunit: Isp1 and Isp2

1. *Synechococcus sp* PCC7942 wild type strain
2. *Synechococcus sp* PCC7942 Trc-Hyn

SEQUENCE LISTING

<160> NUMBER OF SEQ ID NOS: 6

<210> SEQ ID NO 1
<211> LENGTH: 340
<212> TYPE: PRT
<213> ORGANISM: Alteromonas macleodii

```
<400> SEQUENCE: 1

Met Lys Arg Leu Arg Arg Ile Glu Met Ala Leu Pro Thr Leu Asn Lys
1               5                   10                  15

Gln Leu Gln Ala Ser Gly Ile Ser Arg Arg Thr Phe Leu Lys Phe Cys
            20                  25                  30

Ala Thr Thr Ala Ser Leu Leu Ala Leu Pro Gln Ser Ala Val Ala Asp
            35                  40                  45

Leu Ala Thr Ala Leu Gly Asn Ala Arg Arg Pro Ser Val Ile Trp Leu
        50                  55                  60

Pro Phe Gln Glu Cys Thr Gly Cys Thr Glu Ala Ile Leu Arg Ser His
65                  70                  75                  80

Ala Pro Thr Leu Glu Ser Leu Ile Phe Asp His Ile Ser Leu Asp Tyr
                85                  90                  95

Gln His Thr Ile Met Ala Ala Ala Gly Glu Gln Ala Glu Asp Ala Arg
            100                 105                 110

Arg Ala Ala Met Asn Ala His Lys Gly Gln Tyr Leu Leu Leu Val Asp
            115                 120                 125

Gly Ser Val Pro Val Gly Asn Pro Gly Tyr Ser Thr Ile Ser Gly Met
130                 135                 140

Ser Asn Val Asp Met Leu Arg Glu Ser Ala Lys Asp Ala Ala Gly Ile
145                 150                 155                 160

Ile Ala Ile Gly Thr Cys Ala Ser Phe Gly Gly Ile Pro Lys Ala Asn
                165                 170                 175

Pro Asn Pro Thr Gly Ala Val Ala Val Ser Asp Ile Ile Thr Asp Lys
            180                 185                 190

Pro Ile Val Asn Ile Ser Gly Cys Pro Pro Leu Pro Ile Ala Ile Thr
        195                 200                 205

Ala Val Leu Val His Tyr Leu Thr Phe Lys Arg Phe Pro Asp Leu Asp
210                 215                 220

Glu Leu Gln Arg Pro Leu Ala Phe Phe Gly Ser Ile His Asp Arg
225                 230                 235                 240

Cys Tyr Arg Arg Pro Phe Phe Glu Gln Arg Lys Phe Ala Lys Ser Phe
                245                 250                 255

Asp Asp Glu Gly Ala Lys Asn Gly Trp Cys Leu Phe Glu Leu Gly Cys
            260                 265                 270

Lys Gly Pro Glu Thr Phe Asn Ala Cys Ala Thr Val Lys Trp Asn Gln
            275                 280                 285

Gly Thr Ser Phe Pro Ile Glu Ser Gly His Pro Cys Leu Gly Cys Ser
        290                 295                 300

Glu Pro Asp Phe Trp Asp Lys Ser Ser Phe Tyr Gln Ala Leu Gly Pro
305                 310                 315                 320

Trp Glu Trp Tyr Lys Ser Lys Pro Lys Gly Ala Gln Lys His Ala
                325                 330                 335

Gly Lys Asn Ser
            340

<210> SEQ ID NO 2
<211> LENGTH: 369
<212> TYPE: PRT
<213> ORGANISM: Thiocapsa roseopersicina

<400> SEQUENCE: 2

Met Ala Ala Arg Asn Pro Thr Asp Lys Thr Leu Gly Glu Ser Leu Arg
1               5                   10                  15
```

Glu Arg Gly Val Ser Arg Arg Gly Phe Leu Lys Phe Cys Ala Ala Thr
            20                  25                  30

Ala Ser Met Met Ala Leu Pro Pro Ser Met Ala Pro Ala Ile Ala Ala
        35                  40                  45

Ala Leu Glu Gln Ala Lys Arg Pro Ser Val Ile Trp Leu Ser Phe Gln
    50                  55                  60

Glu Cys Thr Gly Cys Thr Glu Ser Leu Thr Arg Ser His Ala Pro Thr
65                  70                  75                  80

Leu Glu Asp Leu Ile Leu Asp Val Ile Ser Leu Asp Tyr His His Thr
                85                  90                  95

Leu Gln Ala Ala Ala Gly Asp Ala Ala Glu His Ala Arg Glu Gln Ala
            100                 105                 110

Met Ala Ala Asn Pro Gly Glu Tyr Leu Val Ile Val Asp Gly Ser Ile
        115                 120                 125

Pro Gly Pro Asp Ser Asn Pro Gly Tyr Ser Thr Val Ala Gly His Ser
    130                 135                 140

Asn Tyr Ala Met Leu Met Glu Thr Val Glu Asn Ala Ala Ala Val Ile
145                 150                 155                 160

Ala Val Gly Thr Cys Ala Thr Phe Gly Gly Leu Pro Gly Ala Asn Pro
                165                 170                 175

Asn Pro Thr Gly Ala Met Ser Val Met Asp Leu Val Lys Asp Lys Pro
            180                 185                 190

Val Ile Asn Val Ser Gly Cys Pro Pro Ile Pro Met Val Ile Thr Gly
        195                 200                 205

Val Ile Ala His Tyr Leu Thr Phe Gly Arg Leu Pro Glu Leu Asp Ala
    210                 215                 220

Tyr Asn Arg Pro Met Ala Phe Phe Gly Gln Ser Ile His Asp Arg Cys
225                 230                 235                 240

Tyr Arg Arg Pro Phe Tyr Asp Lys Gly Leu Phe Ala Lys Thr Phe Asp
                245                 250                 255

Asp Glu Gly Ala Arg Leu Gly Trp Cys Leu Tyr Glu Leu Gly Cys Lys
            260                 265                 270

Gly Pro Thr Thr Tyr Asn Ala Cys Ala Thr Met Arg Trp Asn Asp Gly
        275                 280                 285

Thr Ser Trp Pro Val Glu Ala Gly His Pro Cys Leu Gly Cys Ser Glu
    290                 295                 300

Pro Arg Phe Trp Asp Ala Gly Gly Phe Tyr Asn Thr Val Ser Val Pro
305                 310                 315                 320

Thr Ser Ala Ser Gly Val Asn Val Leu Ala Gly Ala Ala Gly Ala
                325                 330                 335

Ile Val Gly Gly Ala Val Ala Leu Ala Lys Lys Gln Thr Lys Thr
            340                 345                 350

Ala Val Ala His Arg Gln Pro Val Thr Val Glu Glu Leu Glu Ala Lys
        355                 360                 365

Leu

<210> SEQ ID NO 3
<211> LENGTH: 625
<212> TYPE: PRT
<213> ORGANISM: Alteromonas macleodii

<400> SEQUENCE: 3

Met Glu Asn Thr Ala Ser Asn Asn Arg Leu Val Val Asp Pro Ile Thr
1               5                   10                  15

-continued

Arg Ile Glu Gly His Leu Arg Ile Glu Ala Glu Met Asp Gly Asn Thr
    20                      25                  30

Ile Lys Gln Ala Phe Ser Ser Gly Thr Ser Val Arg Gly Ile Glu Leu
            35              40                  45

Ile Leu Gln Gly Arg Asp Pro Arg Asp Ala Trp Ala Phe Ala Gln Arg
50                      55                  60

Ile Cys Gly Val Cys Thr Leu Val His Gly Met Ala Ser Val Arg Ala
65                  70                  75                  80

Val Glu Asp Ala Ile Arg Lys Ala Trp Arg Ser Asn Ala Lys Leu Gly
                85                  90                  95

Val Ala Ile Gly Lys Pro Ser Met Thr Ser Met Pro Lys Gly Pro Met
            100                 105                 110

Gln His Gly Lys Lys Gly His Arg Gln Ser Arg Thr Ser Ile Gly Val
            115                 120                 125

Leu Ser Glu Ala Glu Met Ala Ile Pro Gln Asn Ala Gln Val Ile Arg
130                 135                 140

Asn Ile Met Ile Ala Thr Gln Tyr Val His Asp His Val Met His Phe
145                 150                 155                 160

Tyr His Leu His Ala Leu Asp Trp Val Asp Val Val Ser Ala Leu Asp
                165                 170                 175

Ala Asp Pro Thr Arg Thr Ala Thr Leu Ala Gly Gln Leu Ser Asp Tyr
            180                 185                 190

Pro Arg Ser Ser Pro Gly Tyr Phe Lys Asp Val Lys Gln Lys Val Lys
        195                 200                 205

Thr Leu Val Glu Ser Gly Gln Leu Gly Ile Phe Ser Asn Ala Tyr Trp
    210                 215                 220

Gly His Pro Gly Tyr Lys Leu Pro Pro Glu Val Asn Leu Met Ala Leu
225                 230                 235                 240

Ala His Tyr Leu Asp Ala Leu Thr Trp Gln Arg Glu Val Val Lys Val
                245                 250                 255

His Thr Ile Phe Gly Gly Lys Asn Pro His Pro Asn Phe Val Val Gly
            260                 265                 270

Gly Val Pro Ser Pro Ile Asn Leu Asn Ala Ser Thr Gly Ile Asn Thr
        275                 280                 285

Ser Arg Leu Val Gln Leu Gln Asp Ala Ile Thr Gln Met Lys Ser Phe
    290                 295                 300

Val Asp Gln Val Tyr Tyr Pro Asp Ile Val Ala Ile Ala Gly Tyr Tyr
305                 310                 315                 320

Lys Glu Trp Gly Thr Arg Gly Glu Gly Leu Gly Asn Phe Leu Thr Tyr
                325                 330                 335

Gly Asp Leu Pro Met Thr Ser Met Asp Asp Pro Asp Ser Phe Leu Phe
            340                 345                 350

Pro Arg Gly Ala Ile Leu Gly Arg Asp Leu Ser Lys Val His Asp Leu
        355                 360                 365

Asp Leu Asp Asp Pro Ser Glu Ile Gln Glu Phe Val Ser Ser Ser Trp
    370                 375                 380

Tyr Arg Tyr Ser Gly Gly Asn Ala Ser Gly Leu His Pro Phe Asn Gly
385                 390                 395                 400

Gln Thr Thr Leu Glu Tyr Thr Gly Pro Lys Pro Pro Tyr Lys His Leu
                405                 410                 415

Asn Val Gly Ala Glu Tyr Ser Trp Leu Lys Ser Pro Arg Trp Lys Gly
            420                 425                 430

```
His Ala Met Glu Val Gly Pro Leu Ala Arg Val Leu Met Met Tyr Ala
            435                 440                 445

Lys Lys Asp Ala Ala Gln Asp Ile Val Asn Arg Ser Leu Ser Ile
450                 455                 460

Leu Asp Leu Glu Thr Ser Ala Leu Phe Ser Thr Leu Gly Arg Thr Leu
465                 470                 475                 480

Ala Arg Ala Val Glu Thr Lys Ile Val Val Asn Gln Leu Gln Ser Trp
                485                 490                 495

Tyr Asp Gln Leu Leu Asp Asn Ile Ala Lys Gly Asp Thr Asp Thr Phe
                500                 505                 510

Asn Pro Leu Tyr Phe Asp Pro Thr Asn Trp Pro Ile Lys Gly Gln Gly
                515                 520                 525

Val Gly Val Met Glu Ala Pro Arg Gly Ala Leu Gly His Trp Leu Val
            530                 535                 540

Met Gln Asn Gly Lys Ile Glu Asn Tyr Gln Cys Val Val Pro Thr Thr
545                 550                 555                 560

Trp Asn Ala Gly Pro Arg Asp Pro Asn Ser Gln Ala Gly Ala Tyr Glu
                565                 570                 575

Ala Ala Leu Gln Asp Lys His Thr Leu His Asp Pro Asp Gln Pro Leu
                580                 585                 590

Glu Ile Leu Arg Thr Leu His Ser Phe Asp Pro Cys Leu Ala Cys Ala
                595                 600                 605

Val His Val Met Asp Glu Thr Gly Glu Glu Arg Leu Arg Leu Lys Val
            610                 615                 620

Arg
625

<210> SEQ ID NO 4
<211> LENGTH: 576
<212> TYPE: PRT
<213> ORGANISM: Thiocapsa roseopersicina

<400> SEQUENCE: 4

Met Ser Glu Arg Ile Val Val Asp Pro Val Thr Arg Ile Glu Gly His
1               5                   10                  15

Leu Arg Ile Glu Ala Gln Met Asp Gly Glu Asn Ile Ala Gln Ala Tyr
                20                  25                  30

Ser Ser Gly Thr Ser Val Arg Gly Leu Glu Thr Ile Leu Lys Gly Arg
                35                  40                  45

Asp Pro Arg Asp Ala Trp Ala Phe Ala Gln Arg Ile Cys Gly Val Cys
50                  55                  60

Thr Leu Val His Gly Ile Ala Ser Val Arg Ser Val Glu Asp Ala Leu
65                  70                  75                  80

Lys Ile Glu Leu Pro Pro Asn Ala Gln Leu Ile Arg Asn Leu Met Ile
                85                  90                  95

Ser Ser Gln Phe Val His Asp His Val Met His Phe Tyr His Leu His
                100                 105                 110

Ala Leu Asp Trp Val Asp Val Val Ser Ala Leu Ser Ala Asp Pro Lys
            115                 120                 125

Ala Thr Ser Asp Leu Ala Gln Ser Ile Ser Ser Trp Pro Lys Ser Ser
            130                 135                 140

Pro Gly Tyr Phe Ala Asp Thr Gln Lys Arg Ile Lys Thr Phe Val Glu
145                 150                 155                 160

Ser Gly Gln Leu Gly Ile Phe Ala Asn Gly Tyr Trp Gly His Pro Ala
                165                 170                 175
```

Tyr Lys Leu Pro Pro Glu Ala Asn Leu Met Ala Val Ala His Tyr Leu
        180                 185                 190

Glu Ala Leu Ala Trp Gln Arg Asp Val Ala Arg Leu His Ala Ile Phe
        195                 200                 205

Gly Gly Lys Asn Pro His Pro Asn Phe Val Val Gly Val Pro Ser
210                 215                 220

Pro Ile Asp Ile Asp Ser Asp Ser Ala Ile Asn Ala Lys Arg Leu Ala
225                 230                 235                 240

Glu Val Gln Gln Ile Leu Gln Ser Met Gln Thr Phe Val Asp Gln Val
                245                 250                 255

Tyr Val Pro Asp Thr Leu Ala Ile Ala Ser Phe Tyr Lys Asp Trp Gly
            260                 265                 270

Glu Arg Gly Glu Gly Leu Gly Asn Phe Met Ser Tyr Gly Asp Leu Pro
        275                 280                 285

Ala Thr Gly Thr Met Asp Pro Ala Gln Phe Leu Phe Pro Arg Gly Val
        290                 295                 300

Ile Leu Asn Arg Asp Leu Ser Thr Ile His Glu Ile Asp Leu His Asp
305                 310                 315                 320

Ala Gly Gln Ile Gln Glu Tyr Val Ala His Ser Trp Tyr Glu Tyr Ser
                325                 330                 335

Gly Gly Asn Asp Gln Gly Leu His Pro Tyr Asp Gly Glu Thr Asn Leu
            340                 345                 350

Glu Tyr Asp Ala Arg Gly Gly Val Lys Pro Pro Tyr Thr Gln Leu Asp
        355                 360                 365

Val Asn Asp Gly Tyr Ser Trp Met Lys Ala Pro Arg Trp Lys Gly His
370                 375                 380

Ala Met Glu Val Gly Pro Leu Ala Arg Val Leu Leu Tyr Ala Ser
385                 390                 395                 400

Gly His Glu Gln Thr Lys Glu Leu Val Glu Met Thr Leu Thr Thr Leu
                405                 410                 415

Asp Leu Pro Val Arg Ala Leu Tyr Ser Thr Leu Gly Arg Thr Ala Ala
            420                 425                 430

Arg Thr Leu Glu Thr Lys Ile Leu Thr Asp Thr Ala Gln Asp Trp Tyr
        435                 440                 445

Asn Gln Leu Ile Ala Asn Ile Lys Ala Gly Asp Ser Arg Thr Phe Asn
450                 455                 460

Glu Thr Leu Trp Glu Pro Ser Ser Trp Pro Glu Ala Arg Gly Ala
465                 470                 475                 480

Gly Tyr Met Glu Ala Pro Arg Gly Ala Leu Gly His Trp Ile Val Ile
                485                 490                 495

Lys Asp Arg Lys Ile Ala Asn Tyr Gln Ala Val Val Pro Ser Thr Trp
            500                 505                 510

Asn Ala Gly Pro Arg Asp Pro Ser Asp Gln Pro Gly Ala Tyr Glu Ala
        515                 520                 525

Ala Leu Gln Asp Asn His Gln Leu Val Asp Val Lys Gln Pro Ile Glu
530                 535                 540

Ile Leu Arg Thr Ile His Ser Phe Asp Pro Cys Ile Ala Cys Ala Val
545                 550                 555                 560

His Leu Thr Asp Pro Glu Thr Gly Glu Gln Met Glu Ile Lys Ile Thr
                565                 570                 575

<210> SEQ ID NO 5
<211> LENGTH: 8744

```
<212> TYPE: DNA
<213> ORGANISM: Alteromonas macleodii

<400> SEQUENCE: 5
```

| | | | | |
|---|---|---|---|---|
| aaggtacttc | aaccctattt | ggtatgacac | cgtttcacag | cgcagtgatg | ctcgttttac | 60 |
| tcatatttac | aattgttatg | gtgtatgtgt | atggatttaa | gatgcgcaga | gctgccgcgc | 120 |
| tgctcgaaga | gcttaagtct | actgacaccg | caagcacatc | tgcgccaacg | acaaaagttt | 180 |
| cctctgttgt | cgaatctaat | ccggctgccc | agcagcatgc | ttcggcacct | gcgcaaagta | 240 |
| gcgagccagc | attgtcatcc | actgcctcat | cgcgcaaggg | cacgtttagt | ggcggtatgg | 300 |
| tagtaaccgc | gattttaat | gaaacccatg | atgttaaaac | gttacgtcta | gccagcccag | 360 |
| atggaaaaac | cattccattt | gatttcgaac | caggtcaatt | tgtcacgttc | acactgaaca | 420 |
| tcgatggttt | tgaaaagcca | gttaagcgct | catacaccat | tgcatcatcg | cccactgaac | 480 |
| agtattactt | tgaagttacg | ataaaacgag | aggagttcgg | tgtggtttct | cgttatatgc | 540 |
| atgatgcggt | tgaggtagga | aatacgcttt | caattaaagc | ccccggcggt | aaattttatt | 600 |
| tcaatggtca | tggtgcaaac | agcgttgtgt | tgatttctgg | gggagtgggg | atcacaccga | 660 |
| tgatgagcgc | tgtccgctac | ttaacgacga | cgtgctggga | cggagatatt | tatttctgt | 720 |
| tttgtacgcg | aacgtccaac | gactttattt | ttgagcagga | attaaaatat | ctgcaagcac | 780 |
| gtcaccctcg | gttaaaagta | ctggtcagta | tgactcaagc | agagggtaca | tcctggatgg | 840 |
| gtccccaagg | ccgcttctca | tccgcaatga | taaacgaatt | tgtgccagat | attgcctcaa | 900 |
| aaactgcgca | tatttgtggt | cctcctgcaa | tgatggatgc | aacgaaaaaa | atgctagccg | 960 |
| aattgggtat | gcctgacacg | catattaaaa | ccgaagcgtt | tggggctgct | aaaccaaagc | 1020 |
| ccgcccccgt | taaacctcaa | ttagccacta | acaccaacgc | aggcaacaac | agacaagtac | 1080 |
| ggtttagtct | ttcagacgtc | gaagcccacg | cgggtccgga | tgagaccgta | ttagacgtcg | 1140 |
| ctgatggact | cgatgtagat | atagagaatt | catgcagagc | gggttcgtgc | gggagttgta | 1200 |
| aggtgaaact | gctacgtggt | gacgtcgata | tggaggttga | tgatgggctg | gaacctgaag | 1260 |
| ataagatcag | tgggtatatt | ctggcgtgcc | aagctatccc | taaatctgat | gtggaggttg | 1320 |
| aggcttaatg | aattctcaag | agcgcacaat | tgtaagcagc | ttggttgtcc | taatgatcct | 1380 |
| gctatggctc | ggttttgtat | ggcatagaga | cccagcattc | ccaggcagtt | ttattggatt | 1440 |
| tggcgtgggt | ttaagcgctt | cggtattaat | gcttatccca | ttggtataca | tgatcattaa | 1500 |
| gcgtaacaaa | tcacttaaga | aagtcgtgac | gaagcacatc | gctatgccaa | cgctcctgcg | 1560 |
| tatacatatc | tatgctggtg | tgctggggcc | tattctagcg | ctgatccata | cgcccatcg | 1620 |
| ttttgatagt | gctactggag | tttcgctagt | tatctttatg | atggtcgttg | tgatcagtgg | 1680 |
| gtttgtgggt | cgatatgtac | tcggtcttat | ttcatcgaat | gtgaaagaga | aaaaacgcca | 1740 |
| agtaaatgaa | ctccacgttg | cgctttctaa | cgcaaaacag | gcgttgaaag | acgcagtctg | 1800 |
| tgatgtcaga | tattcgacgt | tgcccaaac | atccgcacga | catattcctt | acattacgtt | 1860 |
| aaatgtgcct | acttcagcac | aaagtaaatt | gttcaaacaa | gaaagccagg | ttctgtccat | 1920 |
| cattgataca | atttccgatg | ttgagtacag | cattctcatt | catgacaccg | cgaaggtgtg | 1980 |
| gtttgctcgt | tggttaaaat | ttcacatcgt | gatttcaatg | acactttatg | tagtcctgtt | 2040 |
| ttttcacatt | ttcagtgaag | tttactttgg | actgcgctgg | ttatgatgaa | atggataata | 2100 |
| atcgttcttg | gcttagttgc | tgctggcttt | ggcgtcagtc | atttcattca | tatgcctgaa | 2160 |
| gatagcgcac | aaattccatg | ggaaaaaatg | gttgaacccg | gttcactcaa | taagcacat | 2220 |

```
gcctttctcg cggatgactg tttgagttgt cacacaccgg tgaagggcgt tgagcgtgac   2280
aaatgtgtgg cgtgtcatgc aaatgatacg catatcgttg cgcgtcaacc cactgcattt   2340
cataccgaca tcaaagaatg tgcaagttgc catgtagagc acaaaggtga atcggccaac   2400
atttcgctca tgagccatat agcgttagtc gacattggtt tcaatatgct ccccaaccca   2460
aatgtcccgt ttgacgaggg cgctgccacc atggcgtttt tggagaacat actagcgaat   2520
aaacaaactc ctgagccctt gtttgtgcac cctgaggtca gtgataaaga agccttatta   2580
aattgtacgc aatgtcacag caacgatgat cgccatttag gtctatttgg agaggattgc   2640
gtgcagtgtc acagcacaga caaatggtca ctgccaaagt ttattcaccc gtcgagtcaa   2700
tcacgtgatt gcaatcaatg tcatgaagcg ccgcccagtc actatatgca gcattttaaa   2760
atgatttccg ccaaagtggc aggcgagcct aaagctaaag ttgaggaatg ctatgcctgt   2820
catcaatcta cgtcctggaa cgatattaag cgtgccggat ggtataaaca ccattaaggg   2880
gtacaaactg tgatcacaaa ttccattgcg ctcgcaacct cggtgctgat cgcaatagta   2940
ttgtttctgc ctcgcttacg acaatctgtc caatggcggg caacagtcac accgttggct   3000
tccattattg gtagcggctt tttgatcatt gcaccactgc tgcattcggt aatggggaaa   3060
tgggctctgc ttggaatagt gttgttgtcc attctggcat atgcgctggg gtcggttatt   3120
cgcttcaata tacgccatgc agaacctgag ctagctagca atcaacaaag cagtattgtg   3180
acgcttgaaa aagcaagtca atgggcgctt ggtgcgcat atgccatttc cgtggcgttt   3240
tatattagtt tgtttgcagc gtttgttttt gatcgtttat caatctctga tacgacgtac   3300
atcaaactgt ttaccagtgg gttgcttgtc atcattacgg tggtcgcttg gctccgtggt   3360 gctaggggc tagagaccat tgagctattc gccgtgacaa taaagttggc tattatagta   3420
ggtgtgctcg cagcgctggc aacctacgac atacaagtac aaagtgcttg gtttcaacat   3480
gaagcgatac aggcattgag ccattttgaa actgttagca tgctcgcagg catgctcatg   3540
gtaacgcaag ggttcgagac aacccgtttt atggggaata actacacgcc agaacagcgc   3600
attaaagcga gtcgttatgc tcagtggatc gctattttc tctatgttgt ttttatcggt   3660
ctaacgtgtc ctatttttct ggattttccg atcacggaat taaacgaaac aacgattagc   3720
tacaccctag ggcaagcaat atgggtattg ccgattttat tactggttgc cgccacggca   3780
agtcaattaa gtgcagcatt agccgatact atcggtggcg gaggcctctt aaaagagctt   3840
ttccatttac ctatctcccc gcaattttac tacgttttag tcatcgccat cgcaggtata   3900
ttagtttggt catccaacgt atttgaaatt attaatctcg cttcaaaagg gtttgcactt   3960
tattacctga tccaaacaat aatcgcggtc aaactcgtga tgcgtcaaag cacaggtcaa   4020
cgcattaggt caacaaaatt acttggtcta tcggtgatcg ttctctgttt attctttgtg   4080
attggctggt caattccagc acctcatagc ttttaaggaa aataccgatg ctatcagtag   4140 aaactcacc agctattgac caaattaaaa atgcggctaa cgctacgct atcattggtg   4200 ttggaaatct attgcagcga gatgatggcg ttggtgtgca cgcggttcgt gctctgcaac   4260
ccctgctaaa gtcttattca aatgtatctt gcattgacgc tgggacactg agctatgaac   4320
ttttggagtg ggttgcgagt tccgatcata cgatagtcat cgacgcggct tatatgcgct   4380
gttcgcctgg tacggtgaga gtgtttgagg acgaggcaat tgcggatcag tttcagcaag   4440
cgacgaccca ttccgttcac cagatcacgt tacgcgatac attgttgacc agccaaacgt   4500
tatattcaaa accttctgcg gtgacgttaa ttggcgtaga gcctgaggcg attgagtggg   4560
gaacctcttt gagtccaaag gtaaatgcag cgttatcatc gatcatcgat atcgcatttg   4620
```

```
cttgcttatc aagcgacgac attcaggcct ataaaccggc aacccaaaag gaggcacgat    4680
gaccgaagaa ctcatttta tgacatccaa tgctgaaaaa accggcaacg taatgccgct     4740
tttgcatcag atacgtcatg cgttgtctca gttaattgaa cgacaagaac aaaccacgat    4800
tgatctgcga cgattgcctt taagcgctag cgaagaagcg cagttagaag cttttcttgg    4860
gcatggagag gttaaagctg atattcaggc gctgggtgat acggtgctaa tcgaatcacg    4920
ctacgcaggc gtttggcttg aaattcacta taacgaagat gtggagatca tgggcaaata    4980
cgttcatatc tgtacctgtc caccaatcat aaaatctcag ccagaagata tggtgttatc    5040
gctcagcaat atagtgtctg acatccattc gttgtctcat caatcttctg atgaaacggc    5100
taaggaggat tgaaatggcg ctaccaacat aaacaagca gttacaagcg tccggtatct     5160
caagacgcac atttcttaag ttttgcgcta caacggcgtc tttactggca ttgccgcaaa    5220
gcgctgttgc cgatttggcg actgcccttg gcaatgcgag aagaccctct gtgatttggt    5280
tgccctttca agagtgcaca gggtgtaccg aagcaatatt gcgctctcat gctcccacat    5340
tggaaagcct tattttcgat catatttcgt tggattatca gcatacgata atggctgctg    5400
cgggagagca agctgaagac gctaggcgtg cggcgatgaa cgcgcacaaa gggcaatatt    5460
tgttgttggt tgatggttcg gttccggtgg gtaacccagg atactcaacg atcagtggca    5520
tgagtaatgt cgatatgctg agagaatcgg caaaagatgc tgcgggtatt attgccatcg    5580
gtacctgcgc gtcttttggc gggatccta aagcaaaccc aaatccgacg ggggcagtgg     5640
cagtaagcga cattattaca gacaagccaa tcgtaaacat ttcaggctgt ccgccactgc    5700
ctatcgcgat tacagctgtg ttggttcatt acctgacgtt taagcgtttc cctgatctcg    5760
acgaattaca acgcccactc gcttttttg gtgaaagcat ccatgacaga tgttatcgac     5820 gcccatttt tgaacaacgt aaatttgcaa aatcgtttga tgatgagggg gcaaaaaatg     5880
ggtggtgttt gttcgaactt ggttgtaaag ggcccgaaac cttaacgca tgtgcaacgg     5940 ttaaatggaa tcaaggcacg agttttccta tcgaatctgg ccatccgtgt cttggttgct    6000
ctgagcccga tttctgggat aaaagcagct tttaccaagc cttgggtcca tgggagtggt    6060
acaaatccaa acccggcaaa ggtgcacaga agcatgctgg gaaaaactca taagataata    6120
ggcaaggctc atggaaaata cagcaagtaa caaccggtta gtcgtcgatc ctatcactcg    6180
aattgaaggg catcttcgaa tagaagctga atggatggg aataccatca acaggcgtt     6240 ctcatcaggc acgtctgttc gggaattga actgatttta caaggcagag atccgcgtga    6300
cgcttgggct tttgcgcaac gtatctgtgg cgtctgcacg ctggtgcatg gtatggcatc    6360
ggtgcgtgct gtcgaagatg caattagaaa agcttggcgg tcaaacgcaa aattaggggt    6420
tgccattgga aagcctcca tgacatctat gccaaaagga ccgatgcaac atggtaaaaa     6480
agggcaccga cagtcacgta cttcaatagg cgtactgagt gaagcagaaa tggctatccc    6540
tcaaaatgca caagtgataa gaaacatcat gattgcaacc caatatgtgc atgatcacgt    6600
gatgcatttt tatcacttgc atgccctaga ttgggttgac gttgtttctg cactagatgc    6660
agatccaacg agaaccgcta cgctcgccgg tcaattgagt gattatcctc gttcatcgcc    6720
gggatatttc aaagatgtga agcaaaaagt caaaacgctg gttgagtctg gcagctagg     6780 gatattcagt aacgcgtatt gggggcatcc tggctataaa ctgccacctg aagttaactt    6840
gatggcatta gcacattatt tagatgcgct aacgtggcag cgtgaagttg taaaagttca    6900
caccatattt ggagggaaaa accctcatcc taattttgtc gttggcggcg tgccttcacc    6960
```

-continued

```
gattaatctc aatgcgtcaa cgggtattaa cacgagtcga ttagtgcaac tacaagatgc    7020
tatcacgcaa atgaagagct tgtcgatca ggtgtattac cccgatattg tggcgattgc    7080
gggttattac aaagagtggg ggacacgagg ggaagggctg ggtaactttc ttacctatgg    7140
agacttacct atgacatcaa tggatgaccc tgattctttc ttgtttccac gaggtgcaat    7200
acttggtcga gacttgagta aagtgcatga ccttgatcta gatgatccct ctgaaattca    7260
agaattcgtc tcttcctcct ggtatcgata tagtggaggg aacgcaagtg gtttacaccc    7320
ttttaatgga caaacaacac tcgagtatac tggtccgaaa ccgccttaca agcacctaaa    7380
tgtaggggct gaatattcat ggttgaaaag tccccgttgg aaaggccatg cgatggaggt    7440
gggaccgctg gctcgcgtgc taatgatgta tgctaaaaaa gatgccgctg cgcaagacat    7500
cgttaatcga tctctttcta tcttggattt agagacctct gcacttttct ccacactcgg    7560
taggacgctc gccagagcag tggaaacaaa aattgtggtt aaccagctac agtcttggta    7620
tgaccaacta ttggataata tcgcaaaggg cgataccgat acgtttaacc ctctgtattt    7680
tgaccctacc aattggccaa ttaaaggcca ggggtaggc gtgatggaag cgcctcgtgg    7740
cgcgttgggg cattggttgg tcatgcaaaa tggcaaaatt gagaattacc aatgtgtcgt    7800
gcctacgaca tggaacgctg gacctcgaga tcccaactca caggcaggtg cttatgaagc    7860
cgctctgcaa gataaacata cgctacatga tcctgaccaa cctttagaga ttttgcgaac    7920
acttcatagt tttgaccccct gcttagcatg tgccgtgcac gtaatggacg aaacagggga    7980
agagcgtttg cgtctaaaag ttcgttaacc ttacttgagg aatattatga aaatcaaaaa    8040
tagtattaga aagtcagtta cttctttaat tgccttttt tatctggtgg taggttcacc    8100
cgttagttat gcgcacccgg gtcatcaagg cgatcattca ctacttttgg gatcgctggt    8160
gtcaacaatc gtgcttgtca ccgttgcgct gtttatttat cgagctagag caagtaggcc    8220
ctatcaacgg gtaaaacagt aatgtgtctc gctatcccca tgaaagtcat tgcaattaaa    8280
ggctttaacg caacgtgtga agcgaaaggt gtctctcgcg aggtgagttt acatttagtg    8340
caagggctag aggtcaaagt tggcgactat gtgatggtac atgttggtta tgctctccaa    8400
gtgatcacct atgatgaagc gcaggtgaca tgggagatgc tcgatcaggt cattgcttac    8460
gatgcatgaa attagtcttt gctatagctt gcttgacaca gtcgctgttc accagcgagc    8520
aaacatgaat aagtctgtca gtctggttca cgtcaaagtc ggcccactgt caggtgttga    8580
gcctgacttg ctgcaccatg cgttcttggc gtgtagaact cacaccattg gcgatcaggc    8640
aacgcttaga attgacacaa gcgctatcaa gatacgctgt aaattgtgtg gcgaattcag    8700
ccgagtttcg gtgaatagta tcctatgtgc aagttgcggt cttt                     8744
```

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agggaggaat aacatatggg atctcgaggc cttaattaac tagtt    45

RECOMBINANT HYDROGEN-PRODUCING CYANOBACTERIUM AND USES THEREOF

CROSS-REFERENCE TO RELATED APPLICATIONS

This application is the national phase of PCT application PCT/US2007/022099 having an international filing date of 16 Oct. 2007, which claims the benefit of priority of U.S. Provisional Application No. 60/851,758 filed 16 Oct. 2006. The contents of these documents are incorporated herein by reference in their entirety.

The invention disclosed herein was made in part with funds from a grant from the United States Department of Energy, Award Number: DE-FG36-05GO15027. The U.S. Government has certain rights in the invention.

BACKGROUND OF THE INVENTION

1. Field of the Invention

The invention relates to a recombinant cyanobacterium comprising an oxygen-tolerant, hydrogen-evolving hydrogenase, and methods of use.

2. Background Information

Cyanobacteria include a large group of photoautotrophic microorganisms. Both cyanobacteria and green algae have attracted considerable attention since they can split water photolytically to produce $H_2$, a clean alternative to gasoline and other fossil fuels. However, one major drawback of this process is that their $H_2$-evolving hydrogenases are extremely sensitive to $O_2$. Thus, to realize its promising potential, a novel $O_2$-tolerant photo-biological system needs to be developed. Transferring $O_2$-tolerant NiFe-hydrogenase into these microbes is one of the approaches currently used to overcome the $O_2$ sensitivity issue. Searching for new $O_2$-tolerant hydrogenases will thus facilitate constructing such photo-biological systems.

The oceans harbor an abundance of microorganisms with H2-production capability, in particular photosynthetic bacteria. Thus far, many of these microorganisms are not identified and their functions remain unknown. These marine microbes are good resources for searching for new genes, such as novel $O_2$-tolerant hydrogenase genes. The J. Craig Venter Institute has an ongoing global ocean microbial sampling expedition, which explores marine bacteria in a culture-independent manner by isolating DNA from ocean samples and transforming it into DNA clones for whole-genome shotgun sequencing. A pilot project for this expedition, conducted in the Sargasso Sea off Bermuda, resulted in the discovery of a total of 1.045 billion base pairs of nonredundant sequences, which are estimated to derive from 1800 genomic species, including 148 previously unknown bacterial phylotypes (*Science*, 304: 66-74, 2004). To take advantage of the environmental genetic information generated in this project, we searched the Sargasso Sea databases for putative NiFe-hydrogenases by using probabilistic modeling approaches such as Hidden Markov Models (HMMs).

Because a large array of genetic techniques are available for cyanobacteria, and their photosystems and $H_2$ evolution systems are well studied, they are attractive candidates for conversion of solar energy into $H_2$. However, nearly all naturally occurring hydrogenases are inhibited by oxygen, which leads to discontinuity of $H_2$ photo-production. Accordingly, there remains a need for a microorganism capable of using solar energy to split $H_2O$ into $H_2$ and $O_2$ in a process that can be carried out in the presence of oxygen.

SUMMARY

A recombinant cyanobacterium comprising an oxygen-tolerant, hydrogen-evolving hydrogenase is provided, wherein the hydrogenase has sufficient activity to produce a measurable amount of hydrogen when the cyanobacterium is incubated aerobically, in the presence of a suitable light source, with water as the feed stock. An example is shown diagrammatically in FIG. 1.

This may be accomplished by identifying novel $O_2$-tolerant hydrogenases and transferring them into cyanobacteria, or by transferring known $O_2$-tolerant hydrogenases into cyanobacteria.

Accordingly, the cyanobacterium comprises an expressible nucleic acid which encodes an oxygen-tolerant, hydrogen-evolving hydrogenase, wherein the hydrogenase can be expressed at an effective level for the production of a measurable amount of hydrogen when the cyanobacterium is incubated aerobically, in the presence of a suitable light source, with water as the feed stock.

Also provided is a genome (e.g. a bacterial genome) comprising an oxygen-tolerant hydrogenase gene, and genes required for oxygenic photosynthesis. In one embodiment, the genome comprises a gene encoding a ferredoxin.

The light source may be solar energy or an artificial source such as, for example, fluorescent light.

In one embodiment, the cyanobacterium is from the group of unicellular cyanobacteria, such as, for example, *Synochocystis* or *Synechococcus*. In another embodiment, the cyanobacterium is from the group of unicellular thermophilic cyanobacteria, such as *Thermosynechococcus elongates* and *Synechococcus ecotypes*.

The oxygen-tolerant, hydrogen-evolving hydrogenase may be from a cyanobacterium or a bacterium other than a cyanobacterium (i.e. the recombinant cyanobacterium may be a hybrid cyanobacterium).

The oxygen-tolerant, hydrogen-evolving hydrogenase may be from a photosynthetic bacterium *Thiocapsa roseopersica*, a marine bacterium *Alteromonas macleodii* and an environmental bacterium *Ralstonia eutropha*. In certain embodiments, the oxygen-tolerant, hydrogen-evolving hydrogenase may be from genetically engineering a native hydrogenase in cyanobacteria.

Also provided is a method for generating hydrogen from water, comprising stably introducing into a cyanobacterium an expressible polynucleotide encoding an oxygen-tolerant, hydrogen-evolving hydrogenase and then culturing the cyanobacterium aerobically, under conditions effective to produce a measurable amount of hydrogen [e.g. in the presence of a suitable light source (e.g. solar energy or fluorescent light) and water].

Further included is a method for generating hydrogen from water, comprising culturing aerobically a cyanobacterium which comprises an oxygen-tolerant, hydrogen-evolving hydrogenase, under conditions which are effective to produce a measurable amount of hydrogen.

In particular embodiments, the method comprises aerobically culturing a hybrid cyanobacterium as described above, under conditions effective to produce a measurable amount of hydrogen.

Also provided is a method for generating hydrogen from water in a bacterium, comprising coupling the photosynthetic machinery of a cyanobacterium to an oxygen-tolerant, hydrogen-evolving hydrogenase.

Further included is a kit comprising a cyanobacterium as described above in a suitable container. The kit may also contain other features desirable to carry out the invention or customarily associated with kits, such as, for example, vessels for culture, reagents for culture in premixed solution or in solid form, instructions, etc.

Furthermore, the invention provides an isolated polynucleotide/nucleic acid encoding an oxygen tolerant hydrogenase. In one embodiment, the polynucleotide comprises the nucleic acid sequence as shown in SEQ ID NO:5, or an active variant thereof, or an isolated polynucleotide whose sequence is at least about 90% identical to the (contiguous) sequence of the nucleic acid sequence as shown in SEQ ID NO:5 (over its entire length).

In yet another embodiment, an expression vector comprising the polynucleotide described above is provided.

Furthermore, a cyanobacterium which comprises the polynucleotide or the expression vector described above and further hereinbelow is provided.

Also provided is an isolated polypeptide having oxygen tolerant hydrogenase activity, for example comprising the amino acid sequence as set forth in at least one of SEQ ID NOS:1-4, or an active variant thereof, or an isolated polypeptide whose sequence is at least about 90% identical to the (contiguous) sequence of at least one of SEQ ID NOS:1-4, (over its entire length).

Furthermore, a method for producing a polypeptide that comprises an amino acid sequence of one of SEQ ID NOS: 1-4, or an active variant thereof, or an isolated polypeptide whose amino acid sequence is at least about 90% identical to a contiguous amino acid sequence of SEQ ID NOS:1-4 (over its entire length), comprising culturing the cyanobacterium as described above and elsewhere herein under conditions effective to produce the polypeptide.

Also provided is a method for generating hydrogen from water comprising culturing the cyanobacterium as described above and elsewhere herein under suitable conditions.

This application claims priority to U.S. provisional application 60/851,758, filed Oct. 16, 2006, which is hereby incorporated by reference.

BRIEF DESCRIPTION OF THE DRAWINGS

FIG. 4. Alignment of AmDE (SEQ ID NO:1) Small Subunit and $O_2$-stable Small subunit HynS (SEQ ID NO:2) (64% identity and 80% similarity).

FIG. 5. Alignment of AmDE (SEQ ID NO:3) Large Subunit ("Novel") and O2-stable large subunit HynL (SEQ ID NO:4) (60% identity 75% similarity) The residues involved in catalytic center are marked in red.

DETAILED DESCRIPTION

Definitions

Figure 1:
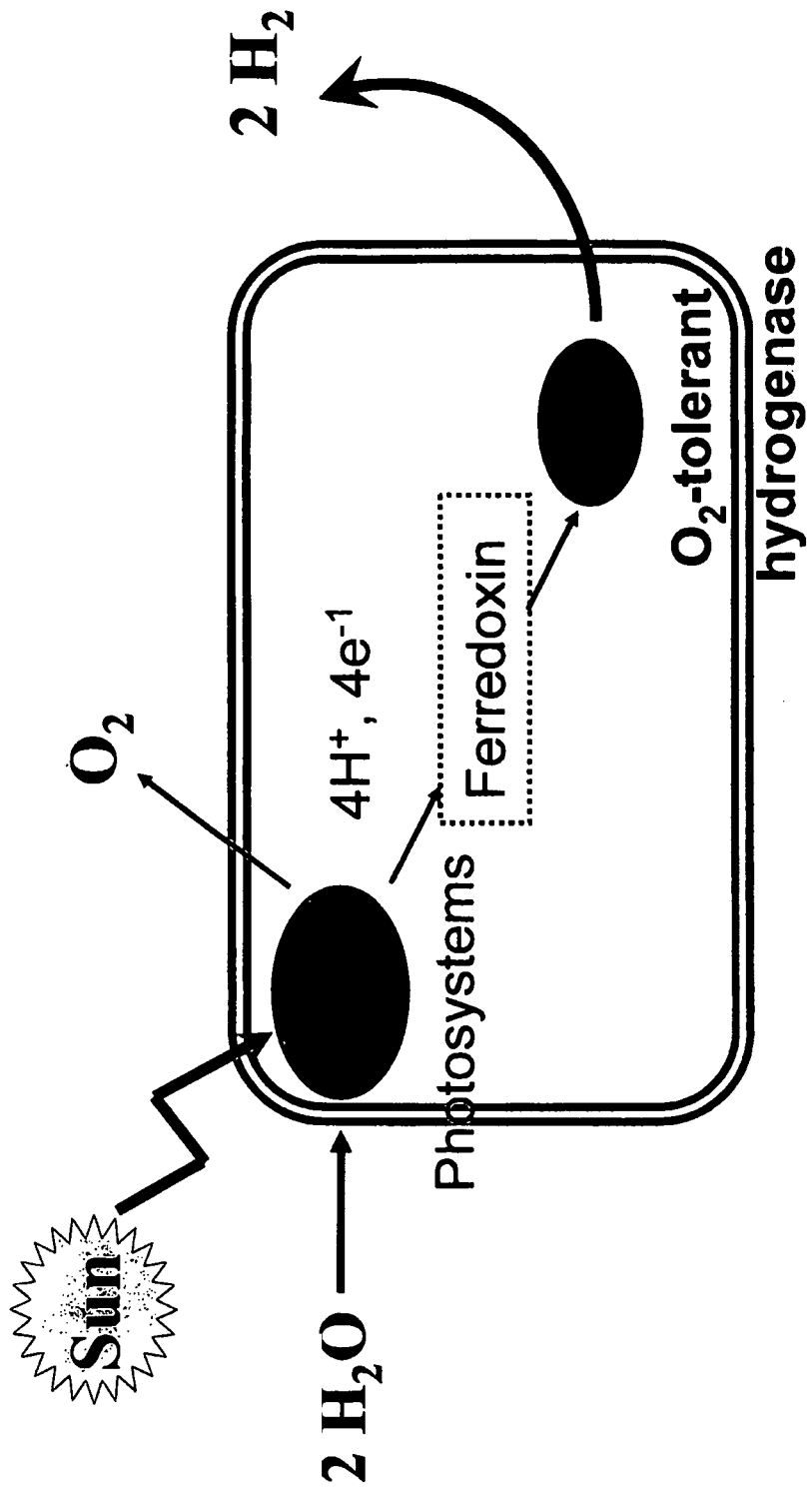
FIG. 1. Cyanobacterium transformed with an $O_2$ tolerant [NiFe]-Hydrogenase

By "hybrid cyanobacterium" is meant, a recombinant cyanobacterium having a hydrogenase of a bacterium other than a cyanobacterium.

By "oxygen tolerant" is meant an organism that is capable of surviving and functioning in ordinary atmospheric $O_2$ (e.g. about 21%), and/or a hydrogenase that is active in atmospheric conditions.

"isp1" refers to a gene for encoding a heterodisulfide reductase that functions as an electron transporter for *Thiocapsa* $O_2$-tolerant hydrogenase Hyn.

"isp2" refers to a gene for encoding a transmembrane protein that is involved in electron transportation for the *Thiocapsa* $O_2$-tolerant hydrogenase Hyn.

"hypC1" refers to a gene for encoding an accessory protein that is essential for maturation of the *Thiocapsa* $O_2$-tolerant hydrogenase Hyn.

"hynD" refers to a gene for encoding a Hyn-specific endoprotease that is involved in processing the large subunit of the *Thiocapsa* $O_2$-tolerant hydrogenase Hyn.

"hupK" refers to a gene for encoding an accessory protein that plays a essential role in assembling the metal cofactor of the *Thiocapsa* $O_2$-tolerant hydrogenase Hyn.

"hypC2" refers to a gene for encoding a chaperon-like protein that is essential for maturation of the *Thiocapsa* $O_2$-tolerant hydrogenase Hyn.

"hypD" refers to a gene for encoding an accessory protein that assembles the metal cofactor in the *Thiocapsa* $O_2$-tolerant hydrogenase Hyn.

"hype" refers to a gene for encoding an accessory protein of the *Thiocapsa* $O_2$-tolerant hydrogenase Hyn.

"hupC/D/H/I/R" refer to accessory genes hupC, hupD, hupH, hupI, and hupR, which are involved in maturation of NiFe-hydrogenases in *Thiocapsa roseopersicina*.

"crtD promoter" refers to the promoter of the gene crtD that is involved in the biosynthesis of photosynthetic pigments in *Thiocapsa roseopersicina*, which is active under photosynthetic growth conditions.

Additional information on gene constructs can be found in Rakhely et al. (1998) J. Bacteriol. 180: 1460-1465; Maroti et al. (2003) Eur. J. Biochem. 270: 2218-2227; Kovacs et (2002) Int. J. Hydrogen Energy 27: 1463-1469; Fodor et al. (2001) Appl. Environ. Microbiol. 67: 2476-2483.

By "active variant" hydrogenase is meant a hydrogenase that contains, e.g., one or more amino acid additions, substitutions, deletions, insertions, inversions, fusions, and truncations or a combination of any of these. Substitutions may be of conservative or non-conservative amino acids. Conservative replacements are those that take place within a family of amino acids that are related in their side chains and chemical properties. These include, e.g., (1) acidic: aspartate, glutamate; (2) basic: lysine, arginine, histidine; (3) nonpolar: alanine, valine, leucine, isoleucine, proline, phenylalanine, methionine, tryptophan; (4) uncharged polar: glycine, asparagine, glutamine, cysteine, serine, threonine, tyrosine; (5) aliphatic: glycine, alanine, valine, leucine, isoleucine, serine, threonine, with serine and threonine optionally be grouped separately as aliphatic-hydroxyl; (6) aromatic: phenylalanine, tyrosine, tryptophan; (7) amide: asparagine, glutamine; and (9) sulfur-containing: cysteine and methionine (see, for example, Biochemistry, 2nd ed., Ed. by L. Stryer, W H Freeman and Co.: 1981). Whether a change in the amino acid sequence of a peptide results in an active variant can be readily determined by assessing the ability of the variant to exhibit hydrogenase activity in a fashion similar to the wild-type hydrogenase. Peptides in which one or more additions, deletions or substitutions have been introduced can be readily tested. Polynucleotides encoding such variants are included within the intended scope. Preferably such active variants are at least 80%, more preferably 90%, and even more preferably 95%, 96%, 97%, 98% or 99% identical to the "wild-type" hydrogenase. Preferably an active variant exhibits at least 50% of the activity of the wild-type hydrogenase under similar conditions, more preferably 55%, 60%, 65%, 70%, 75%, even more preferably 80%, 85%, 90%, 95%, 100%.

Methods

Figure 2:
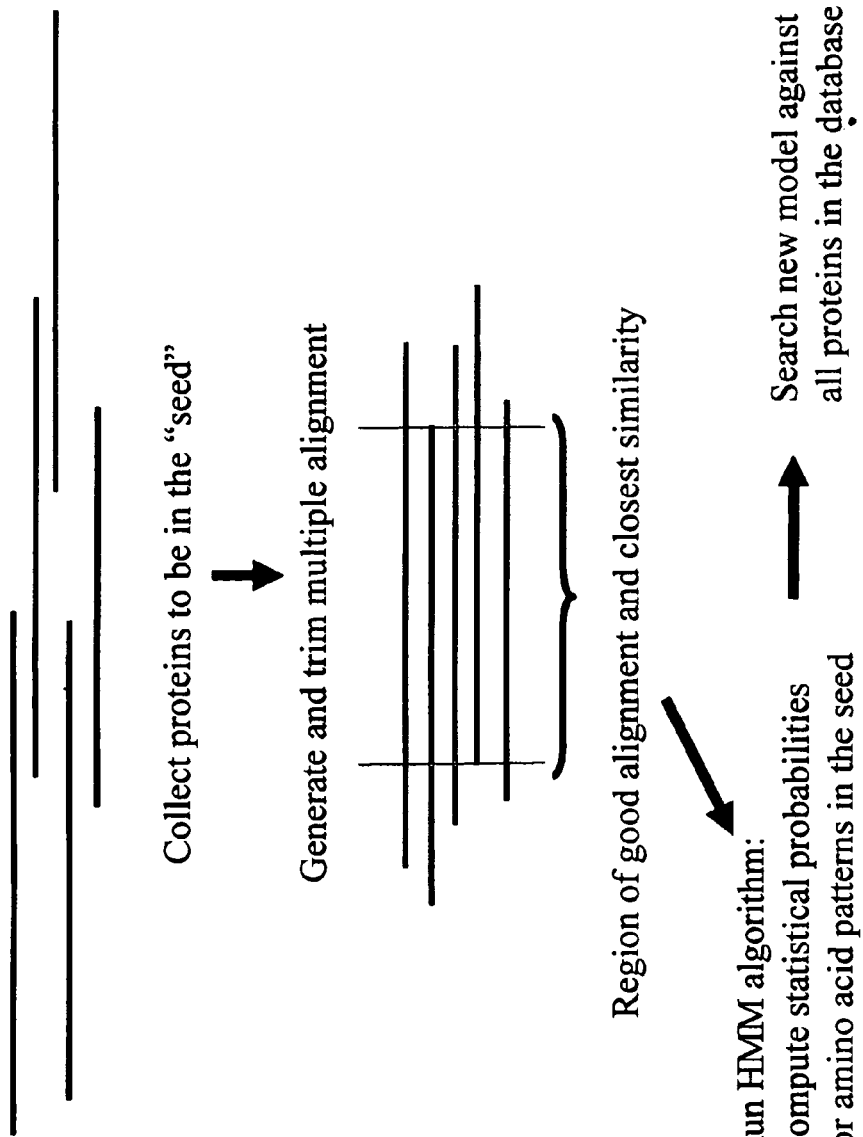
FIG. 2. Building Hidden Markov Models (HMMs)

Hidden Markov models were constructed as shown in FIG. 2. (A detailed description may be found in Durbin et al. (1998) Biological Sequence Analysis: Probabilistic Models of Proteins and Nucleic Acids analysis. Cambridge University Press.) Briefly, known hydrogenases having the desired properties were collected and compared for regions of close similarity, sequences were "trimmed" to core regions of good alignment and closest similarity, and the protein database was searched for potential candidates having identity or close similarity to the core region.

Hydrogenase Activity Assay:

$H_2$-Evolution activity assay was carried out using the artificial electron donor methyl viologey ($MV^+$). Shown below is the chemical structure of methyl viologey dichloride ($MV^{2+}$ $2Cl^-$), a methyl viology in oxidized form.

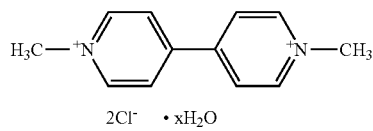

$2H^+ + 2MV^+$ (reduced form, blue) is transformed into $H_2 + 2MV^{2+}$ (oxidized form, colorless) in the presence of hydrogenase. The details procedures for this assay are listed below. First, the reaction components, potassium phosphate buffer (pH 7.0, 25 µM), methyl viologen (2 uM), crude cell extracts and/or purified hydrogenase (20-200 µg protein/ml), are added into a sealed serum bottle. After gasing the bottle with argon for 15 minutes, sodium dithionite (final concentration 5 mM) is added to the reaction system to convert methyl viologey from the oxidized from to the reduced form, which initiates the redox reaction. 30 minutes later, $H_2$ evolution can be quantitatively measured using gas chromatography (GC). Alternatively, $H_2$ evolution can be quantitatively measured using a Clark Electrode System.

An additional method for hydrogen evolution activity assay is to use reduced ferredoxin as an electron donor, which is directly linked to photosynthesis systems PS I and PS II. In a reaction system composed of 20 mM MES buffer, cyanobacterial ferredoxin (10 ug/mml), purified PS I/11 systems (~100 µg protein/ml), and hydrogenase samples (20-200 µg protein/ml), light is applied to initiate the reaction, in which electrons generated by photosynthesis are transferred to ferredoxin, and then transferred to the hydrogenase for hydrogen evolution. $H_2$ evolution in this system can be quantitatively measured using a Clark Electrode System.

Hydrogen uptake activity assay was carried out using the artificial electron receptor benzyl viologey ($BV^{2+} 2Cl^-$). Shown below is the structure of benzyl viologey dichloride ($BV^{2+} 2Cl^-$), a benzyl viologey in oxidized form.

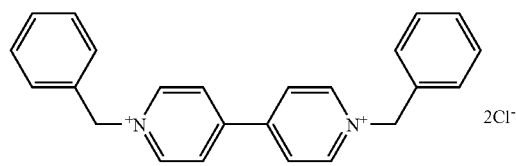

$2BV^{2+} 2Cl^-$ (colorless)+$H_2$ is transformed to $2BV^+Cl^-$ (blue)+2HCl in the presence of hydrogenase. The color changes are quantitatively measured, for example, using a spectrophotometer. The reaction was carried out in the presence of potassium phosphate buffer (pH 7.0, 20 µM), benzyl viologen (2 µM), crude cell extracts (20-200 µg protein/ml), and 10% $H_2$.

Methods for preparing recombinant microorganisms are described inter alia, in Sambrook et al., Molecular Cloning: A Laboratory Manual Cold Spring Harbor Laboratory Press (2001) and Thiel, T., Chapter 19: Genetic analysis of cyanobacteria, in "The Molecular Biology of Cyanobacteria" edited by D. A. Bryant. P. 582-606, Kluwer Academic Publishers (1994).

Example 1

Selection of Potential H$_2$ases for Construction of Hybrid Cyanobacterium

The sequences of 96 large subunits and 85 small subunits of known NiFe-hydrogenases were collected as seeds (i.e. prototypes). Based on these seeds, seven HMMs were built for hydrogenase large subunits and seven HMMs were built for small subunits. The 14 NiFe-hydrogenase HMMs were searched against 1.2 million peptide sequences of the Sargasso Sea microbes, and 20 peptide hits representing the sequences from 10 NiFe-hydrogenases were identified. 11 peptide hits came from hydrogenase large subunits, and 9 peptide hits came from small subunits. Three of 10 NiFe-hydrogenases are known hydrogenases:

*Shewanella oneidensis* quinone-reactive hydrogenase (8 hits)
*Citrobacter freundii* hydrogenase (2 hits)
*E. coli/S. enterica* hydrogenase (1 hit)

The remaining 7 NiFe-hydrogenases appear to be novel, with homology to

E. coli/S. enterica hydrogenase-2 (3 hits)
E. coli/S. enterica hydrogenase-3 (1 hit)
E. coli/S. enterica hydrogenase-4 (1 hit)
Gloeothece sp. uptake hydrogenase (1 hit)
Thiocapsa roseopersicina $O_2$-stable hydrogenase (3 hits)

Example 2

Figure 3:
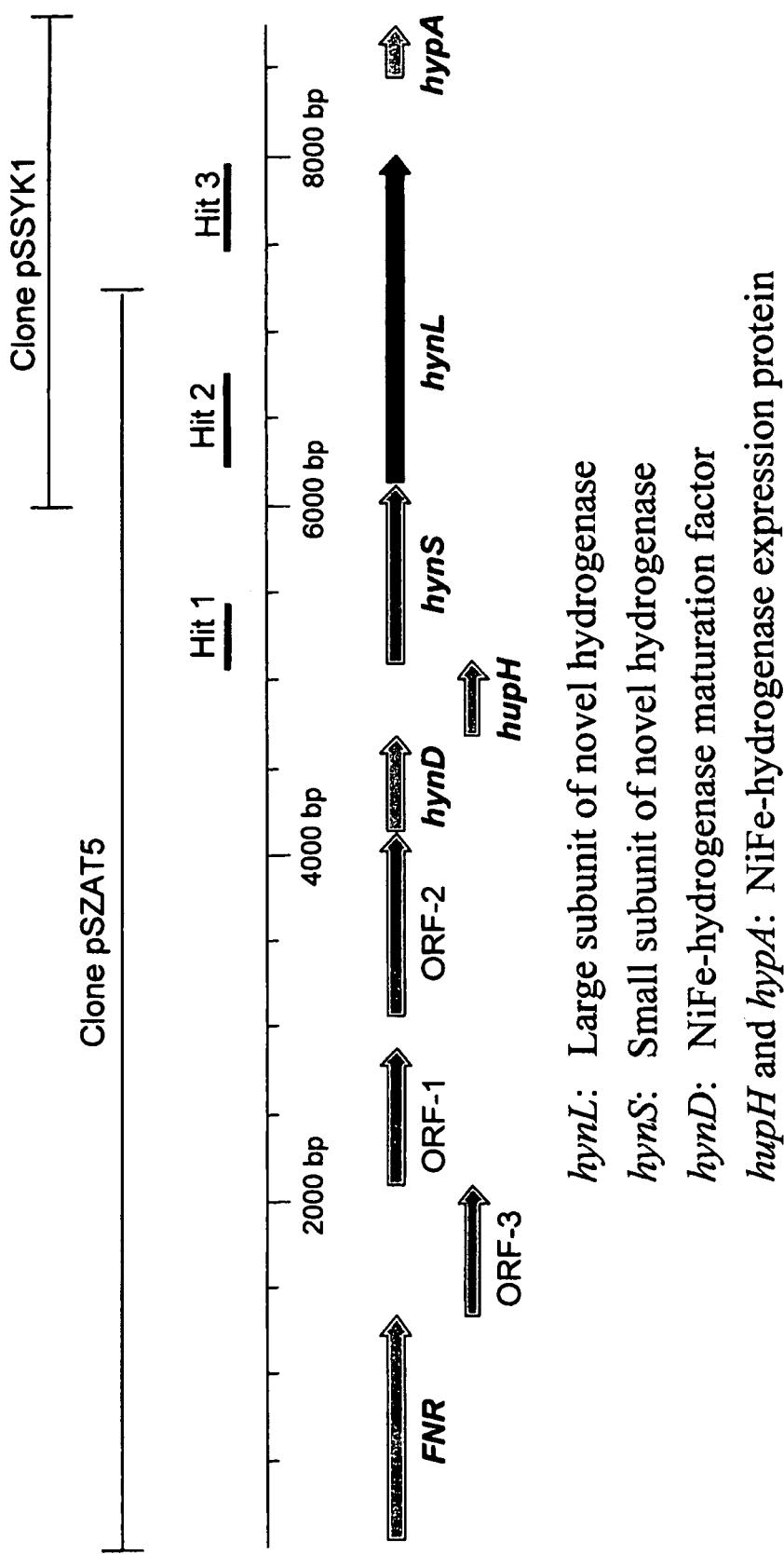
FIG. 3. Cloned genes of a putative novel hydrogenase from the Sargasso Sea with strong homology to a *Thiocapsa* $O_2$-stable hydrogenase (60-64% identity and 75-80% similarity)

Expression of A. macleodii Hydrogenase in T. roseopersicina Using a Broad Host Range Vector A hydrogenase from Example 1 with a strong homology to a Thiocapsa $O_2$-stable hydrogenase (60% identity and 75% similarity) was cloned and heterologously expressed in Thiocapsa roseopersicina, as shown diagrammatically in FIG. 3. This hydrogenase was subsequently shown to be 100% identical to Alteromonas macleodii hydrogenase.

The host organism, Thiocapsa roseopersicina, is a wild-type strain that contains 3 different hydrogenases, wherein hydrogenase biosynthesis is understood in detail. A suitable mutant (ΔhynSL, ΔhupSL, ΔhoxH) was constructed, and transfected with pAmDHSL, an expression vector for the expression of hynD hupH hynS hynL from Alteromonas macleodii in the Sargasso Sea (hynS and hynL are the structural genes of the A. macleodii hydrogenase, whereas hynD and hupH are two of its accessory genes). This vector can self-replicate in T. roseopersicina and the gene expression in this vector is under the control of crtD promoter (Fodor et al., 2004, Appl Environ Microbiol. 70(2):712-21). Thus, expression of hynD hupH hynS hynL in the Thiocapsa mutant can be induced by tungsten light.

Figure 6:
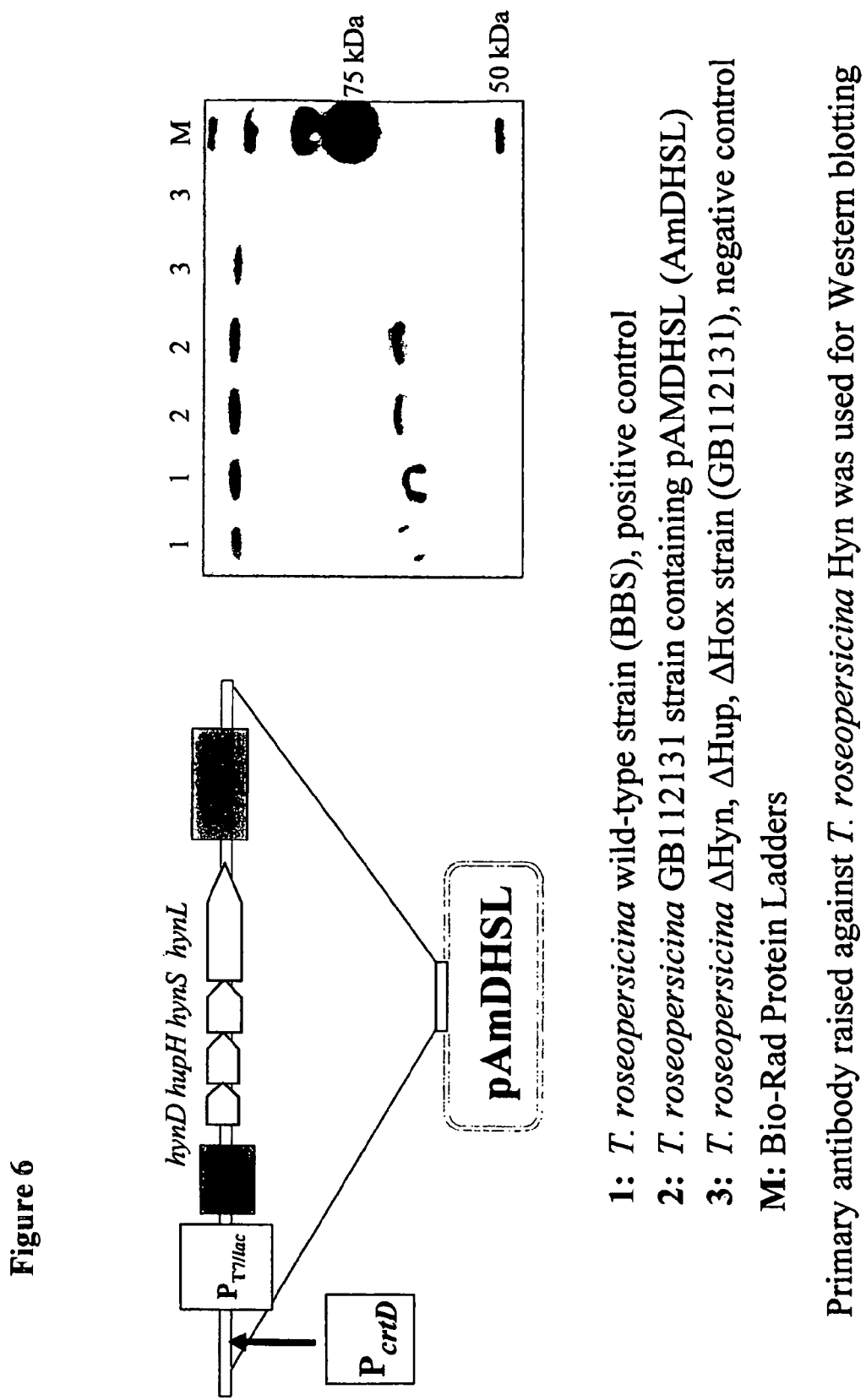
FIG. 6. *Alteromonas macleodii* hydrogenase is hetero-expressed in *Thiocapsa roseopersicina*
Figure 7:
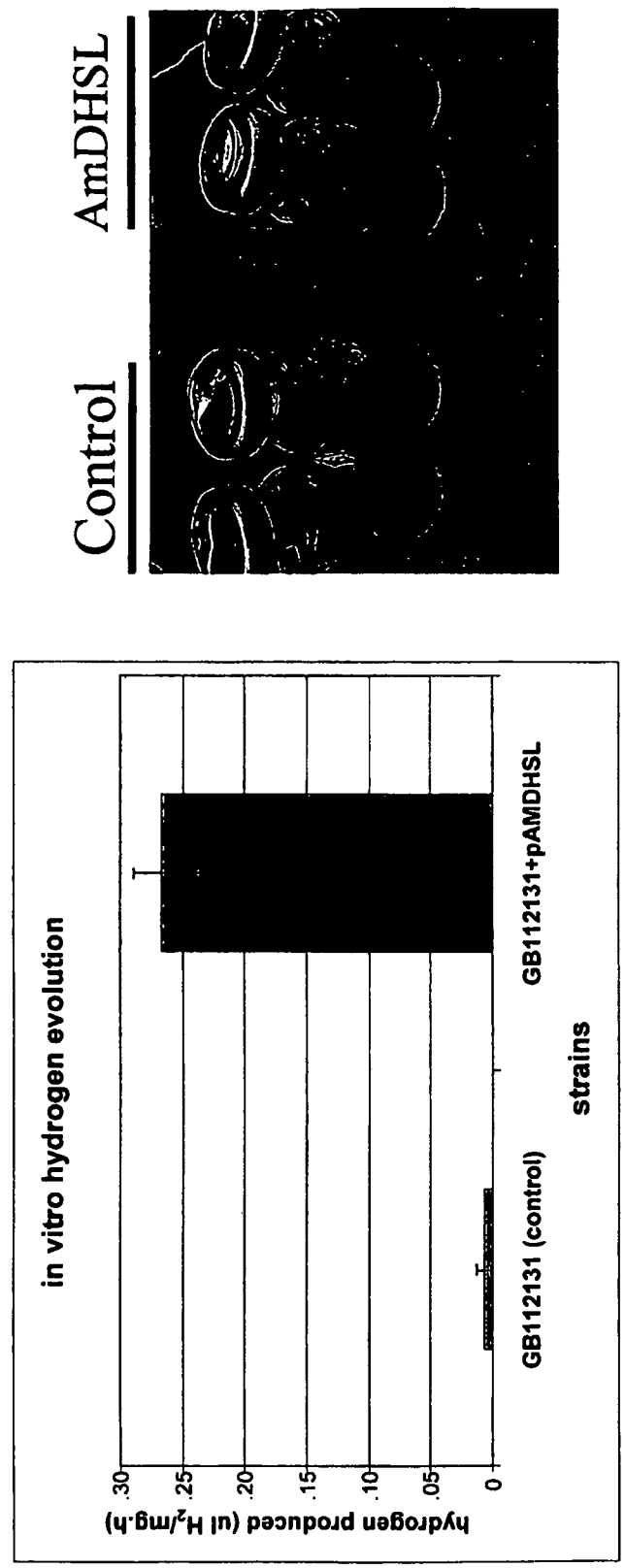
FIG. 7. Heterologously expressed A.M. hydrogenase is active under in vitro conditions. Detection of hydrogen evolution activity using Gas chromatography method.

As shown in FIG. 6, Alteromonas macleodii hydrogenase is hetero-expressed in Thiocapsa roseopersicina. In this experiment, we raised rabbit polyclonal antibody that specifically reacts with T. roseopersicina $O_2$-tolerant hydrogenase large subunit HynL, and used it as a primary antibody for Western blotting. As the result shows, this antibody not only reacts with the T. roseopersicina HynL (~64 Kda) but also with A. macleodii HynL (~69 KDa) because two hydrogenases have similar protein sequences. The activity of heterologously expressed enzyme was further determined by $H_2$-evolution and $H_2$-uptake activity assays as described above. The results (FIG. 7) show the heterologously expressed enzyme is functional under in vitro conditions, and this enzyme is capable of producing hydrogen in an oxygen containing environment. $H_2$ uptake activity was also found in this enzyme.

Example 3

Figure 8:
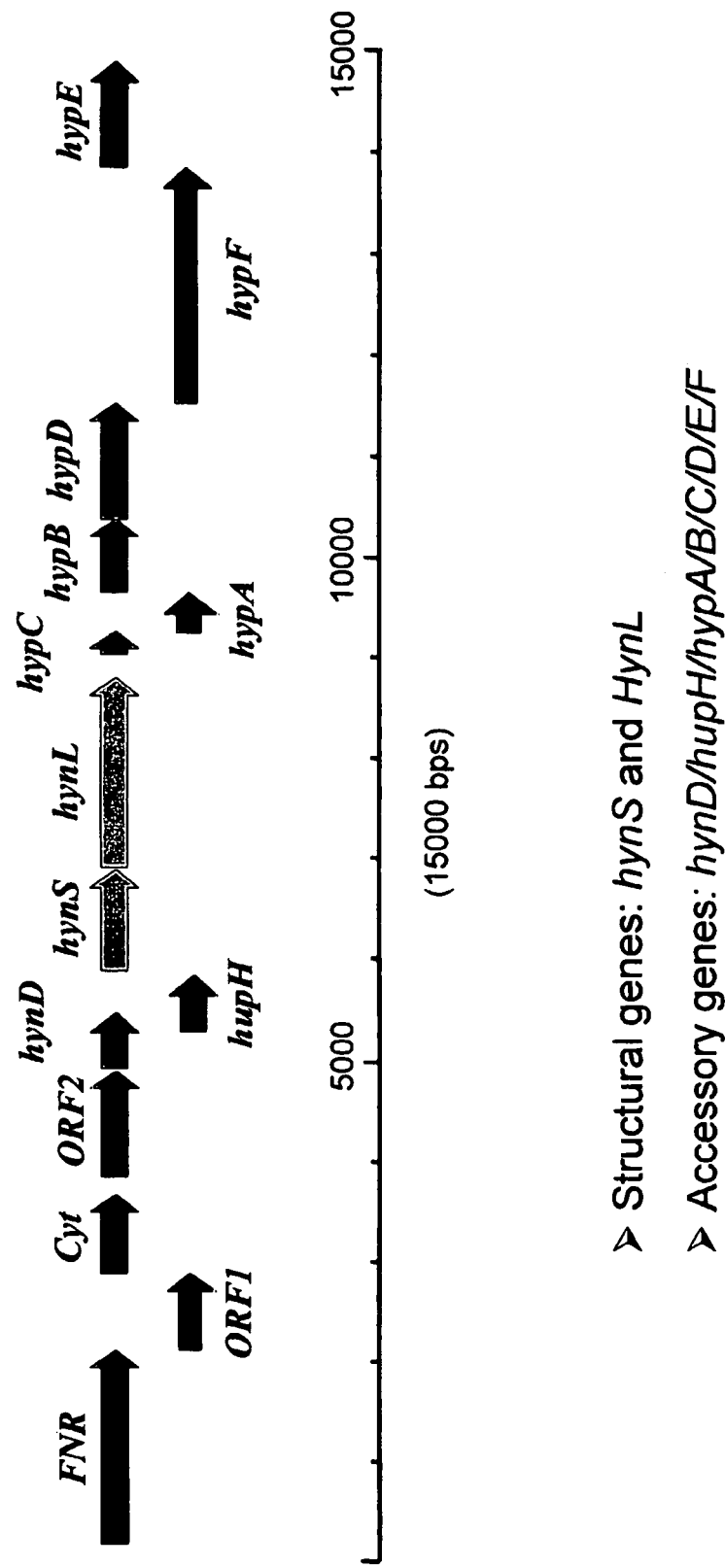
FIG. 8. Sargasso Sea Hydrogenase with 100% identity to native hydrogenase Hyn in *Alteromonas macleodii*.

Characterization of Native NiFe-Hydrogenase from Marine Bacterium Alteromonas macleodii Alteromonas macleodii (strain deep ecotype, "AmDE") is one of 135 marine microbes sequenced at Venter Institute. It is a gram-negative, heterotrophic marine bacterium that grows under aerobic conditions. The Alteromonas macleodii strain deep ecotype (AmDE) was isolated from deep water (3500 meters) in Uranian Basin (Crete, Ionian), has an optimal growth temperature of 20° C., and contains only one hydrogenase in its genome. (In contrast, Alteromonas macleodii strain 107 (Am107) from the ATCC was isolated from superficial water in the Pacific Ocean (Oahu, Hi.), has an optimal growth temperature of 20° C., and contains no hydrogenase.) The hydrogenase is illustrated in FIG. 8.

Figure 9:
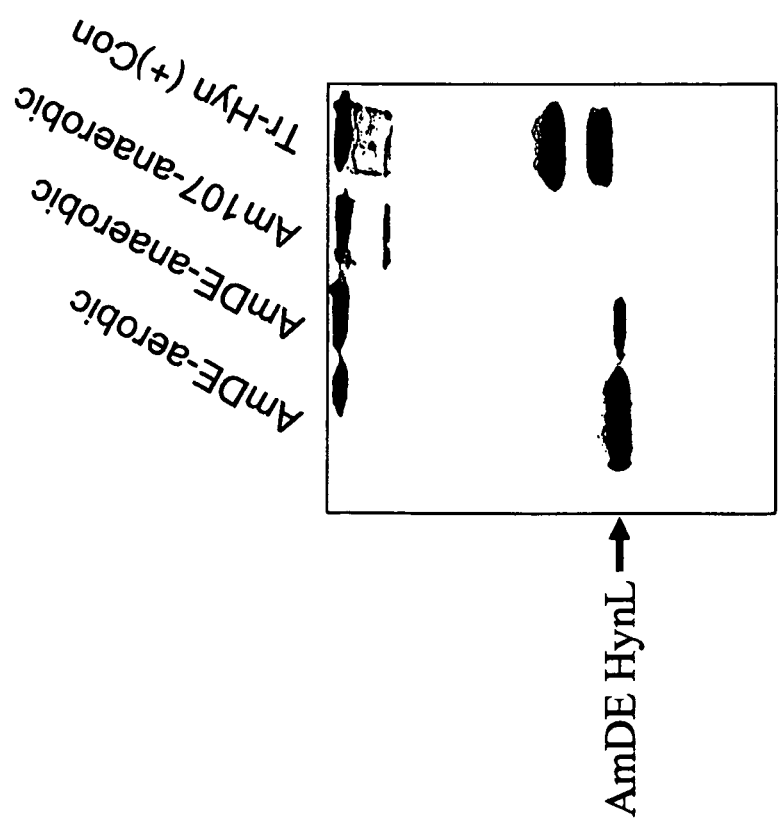
FIG. 9. Expression of native hydrogenase in AmDE. Crude cell extracts and rabbit serum specific for $O_2$-stable hydrogenase Tr-Hyn were used for Western blotting.

AmDE was grown under aerobic (in the air, 28° C.) and anaerobic (in argon, 28° C.) conditions for 12 hours, and cells were harvested through centrifugation and then sonicated. The sonicated cell suspensions were subjected centrifugation and the resulting crude cell extracts were used for Western blotting. Rabbit polyclonal antibody specific for the large subunit HynL of T. roseopersicina $O_2$-tolerant hydrogenase (Tr-Hyn) was used as a primary antibody, and HRP-conjugated goat serum specific for rabbit IgG was used as a secondary antibody. The results showed that AmDE hydrogenase was expressed in much higher amounts under aerobic conditions as compared to anaerobic conditions (FIG. 9). In experiments at varying temperatures, more hydrogenase was detected in AmDE cells grown at 28° C. than lower temperatures. In contrast, no hydrogenase was detected in strain Am107.

Native hydrogenase Hyn of AmDE was purified over a DEAE 52 column. Briefly, Alteromonase macleodii cells were harvested from 1.5 liters of culture by centrifugation and they were sonicated in 10 mM Tris HCl (PH 8.0) buffer. After cell debris was removed by centrifugation, the supernatant was loaded on a DEAE 52 Cellulose Column, which was then eluted with 0-0.6 M NaCl gradient according to manufacturer's standard procedures http://www.whartrnan.com/ <URL: www.whatman.com.html>. The hydrogenase Hyn in eluted fractions was detected by $H_2$-Evolution activity assay, in which methyl viologey dichloride was used as artificial electron donors (method described hereinabove). The results showed that the Hydrogenase Hyn of AmDE was eluted from the column at 0.4 M NaCl.

A. $H_2$-Evolution Activity and Uptake Activity $H_2$-Evolution Activities of native hydrogenase in AmDE (AmDE-Hyn) as measured by gas chromatography, were as follows:

Tr-Hyn (Positive Control): 49.10 nmoles $H_2$/min/mg protein
DEAE 52-Purified AmDE-Hyn: 24.41 nmoles $H_2$/min/mg
AmDE-Hyn in crude extract: 1.74 nmoles $H_2$/min/mg Hydrogen uptake activity was measured using the Artificial Electron Receptor Benzyl viologey dichloride. Results are shown in Table 1.

TABLE 1

| | Samples | | |
|---|---|---|---|
| | Tr-Hyn (Thiocapsa $O_2$-stable hydrogenase) | AmDE-Hyn (AmDE hydrogenase) | Am107 crude extract (-) Control |
| Reaction Time needed | 70 min (at 55° C.) 140 min (at 37° C.) | 5 Hrs (at 55° C.) 24 Hrs (at 37° C.) | No |
| $H_2$-uptake activity | 1608 nmole $H_2$/min/mg | 130.5 nmole $H_2$/min/mg | 0 |

B. Thermal Stability of AmDE Hydrogenase (AmDE-Hyn)

Thermal stability of AmDE-Hyn and Tr-Hyn were compared. Hydrogenase samples (AmDE-Hyn or Tr-Hyn) were equally divided into three fractions, and these fractions were treated separately under the conditions listed below, followed by assay of hydrogenase activity (1) Untreated (keep samples on ice for two hours)
(2) Treat samples at 70° C. for two hours
(3) Treat samples at 85° C. for two hours The following values are based on $H_2$ evolution:
Relative Activity of Heat-Treated Tr-Hyn*:
Tr-Hyn un-treated: 100.0%
Tr-Hyn treated at 70° C.: 75.0%
Tr-Hyn treated at 85° C.: 43.2%

Relative Activity of Heat-Treated AmDE-Hyn*:
AmDE-Hyn un-treated: 100.0%
AmDE-Hyn treated at 70° C.: 93.3%
AmDE-Hyn treated at 85° C.: 76.6%
*The activities of untreated hydrogenases, Tr-Hyn and AmDE-Hyn, were considered as 100%, and the activities of heat-treated. Hydrogenases were normalized using untreated hydrogenases as standards.

TABLE 2

Thermal stability of $H_2$ uptake activity of AmDE NiFe-hydrogenase
Relative $H_2$-Uptake Activity
(uptake rate nmoles $H_2$/min/mg/protein)

| Tr-Hyn (*Thiocapsa* O2-stable hydrogenase Hyn) | AmDE-Hyn (*Alteromonas* hydrogenase Hyn) |
|---|---|
| Untreated: 100% (402.6) | Untreated: 100% (32.0) |
| 70° C.: no activity | 70° C.: 103% |
| 85° C.: no activity | 85° C.: 83.4% |

Overall, these results show that this hydrogenase AmDE-Hyn has extraordinary thermostability and is even more thermostable than known stable hydrogenase Tr-Hyn.

C. Oxygen-Stability of AmDE NiFe-Hydrogenase (AmDE-Hyn)

Air (21% $O_2$) was used to test AmDE-Hyn's $O_2$-stability. AmDE-Hyn was purified from *Alteromonase macleodii* at room temperature in the air, and purified AmDE-Hyn was stored in the air for 45 days. The effect of $O_2$ on hydrogenase stability was determined by performing $H_2$-evolution activity assays on AmDE-Hyn that were stored in the air for different times. The results are shown in Table 3.

TABLE 3

Examination of Oxygen-stability of Novel
AmDE NiFe-hydrogenase (AmDE-Hyn)

| | Time that AmDE-Hyn was stored in the air | | |
|---|---|---|---|
| | Day 1 | Day 14 | Day 45 |
| $H_2$-Evolution activity (two independent assays were performed at each time point) | 100% (2994) 100% (2676) | 98% (2938) 104% (2799) | 101% (3016) 99% (2654) |

These results show that AmDE-Hyn's hydrogenase activity was unchanged after being stored in the air for 45 days, indicating that it is a highly $O_2$-stable hydrogenase Example 4

Figure 10:
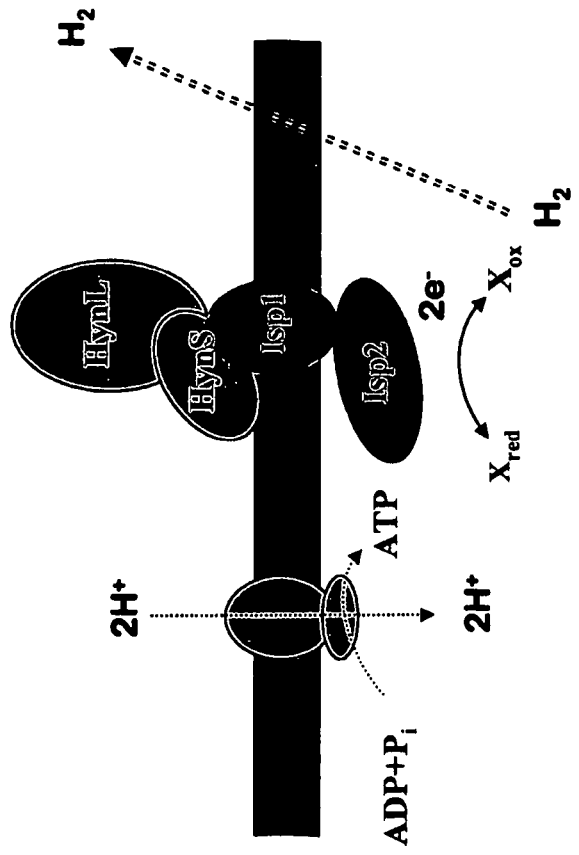
FIG. 10. Phototrophic purple sulfur bacteria *Thiocapsa roseopersicina* carries an $O_2$-tolerant hydrogenase (Hyn).

Transferring a Known $O_2$-Tolerant NiFe-Hydrogenase from Other Photosynthetic Bacteria into Cyanobacteria Phototrophic purple sulfur bacteria *Thiocapsa roseopersicina* carries an $O_2$-tolerant hydrogenase (Hyn) with high $O_2$ and thermal stability, and resistance to proteolysis, and having 2 structural subunits, HynS and HynL, and 2 electron transfer subunits, Isp1 and Isp2, as shown in FIG. 10. This hydrogenase has a $T_{1/2}$ of 6 days when stored in air (*Biochimica et Biophysica Acta* 523:335-343 (1978).

Figure 11:
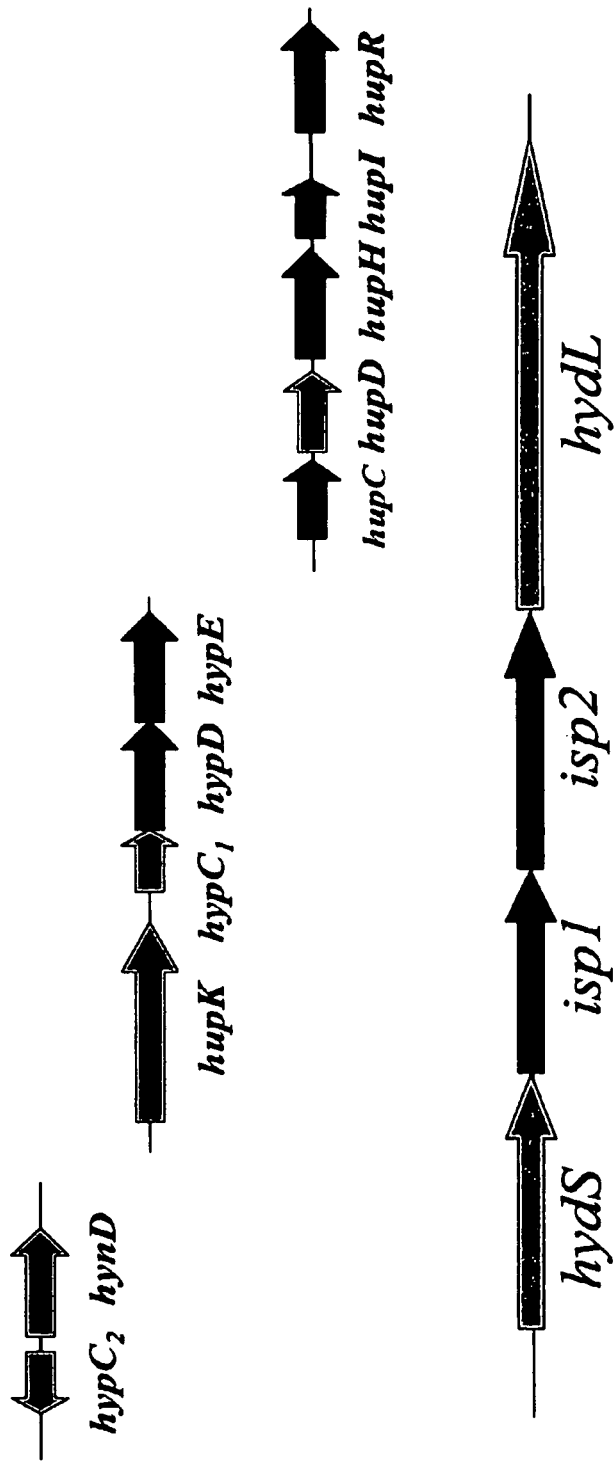
FIG. 11. Genes for encoding and assembling *T. roseopersicina* $O_2$-tolerant hydrogenase.
Figure 12:
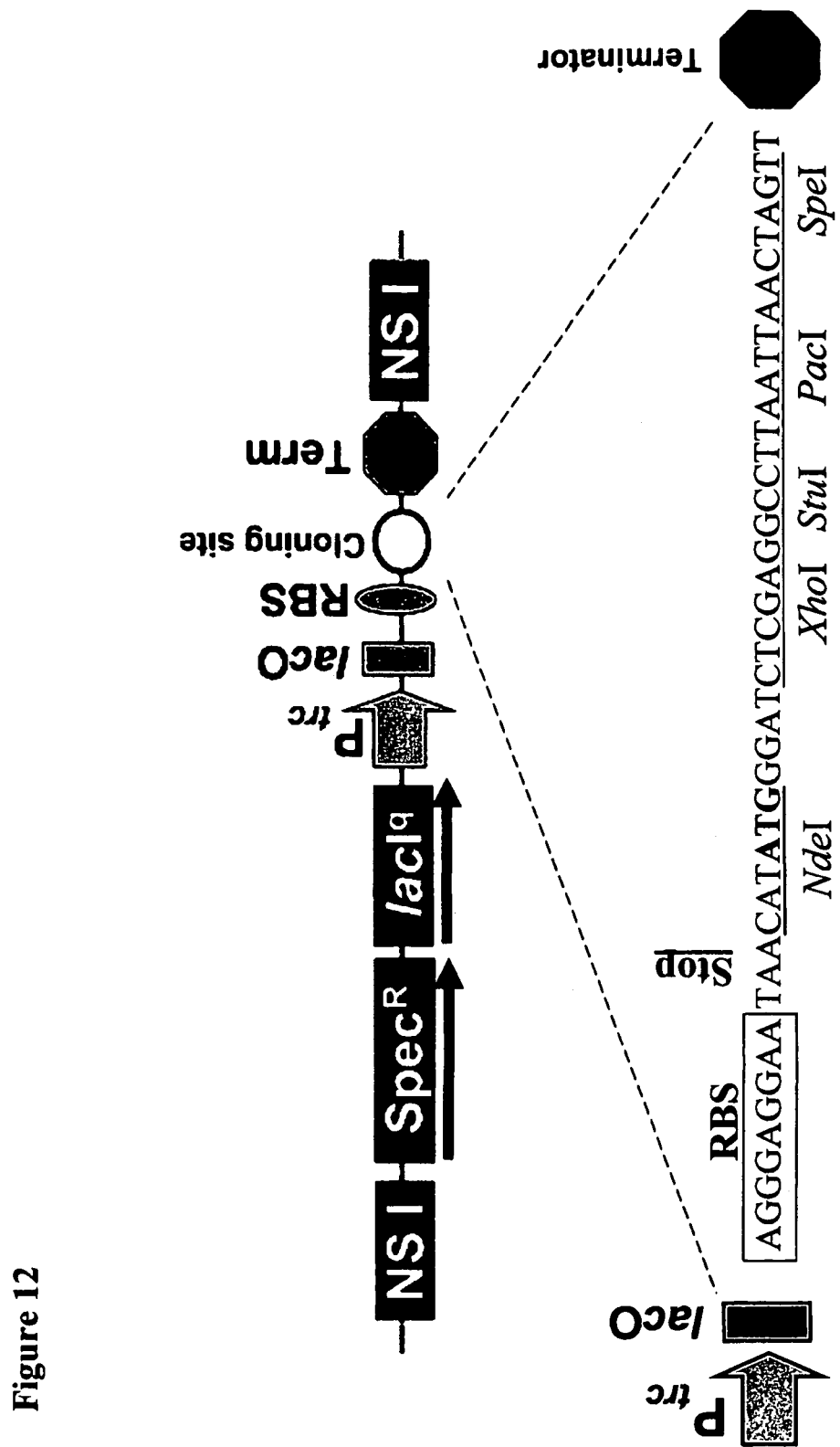
FIG. 12. IPTG-inducible Expression Vector pTrc-NSI (Targeting the Neutral Site I Region) was used for transferring hydrogenase genes into cyanobacterium *Synechococcus* sp PCC7942. NS I: neutral site I region in *Synechococcus* sp PCC7942; SpecR: spectinomycin resistance cassette; Ptrc: an IPTG-inducible promoter; lac1q: gene expression cassette of repressor Lac1q; lacO: lac operator sequence; RBS: ribosomal binding site; Term: transcription terminator, cloning site (SEQ ID NO:6), lacO to terminator.

The genes for encoding and assembling *T. roseopersicina* $O_2$-tolerant hydrogenase are shown in FIG. 11. These include structural genes hydS and hydL, electron-transfer elements: isp1 and isp2, and accessory genes hypC1, hynD, hupK, hypC1, hypD, hypE, and hupC/D/H/I/R IPTG-inducible Expression Vector pTrc-NSI (Targeting the Neutral Site I Region) (Xu Y., T. Mori, and C. H. Johnson. 2003, EMBO J. 22(9):2117-26.) was used for transferring hydrogenase genes into cyanobacterium *Synechococcus* sp PCC7942 (a strain we obtained from ATCC, <URL:www.atcc.org.html>), as shown in FIG. 12.

Figure 13:
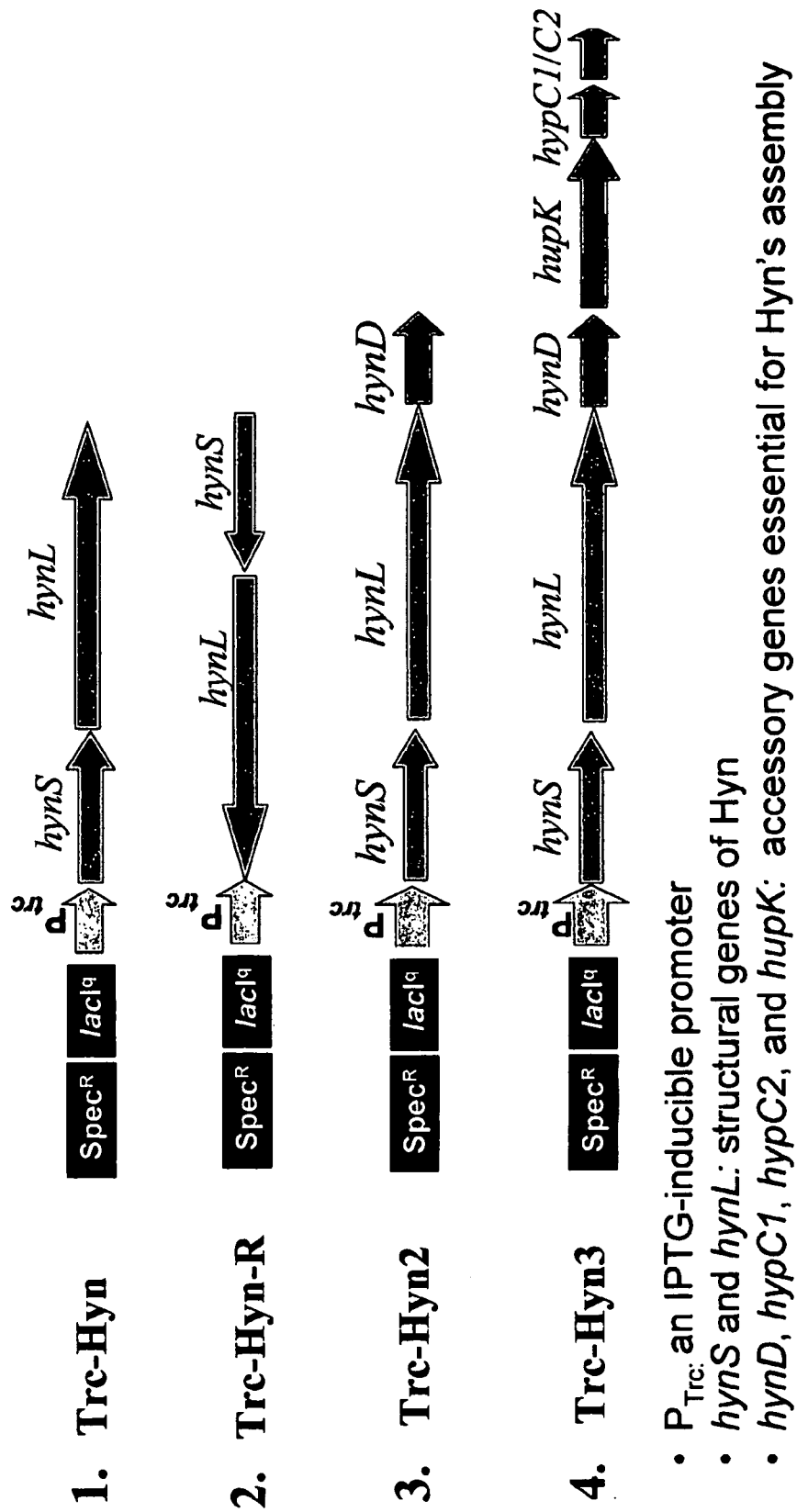
FIG. 13. Constructed recombinant *Synechococcus* PCC7942 strains with Hyn's genes integrated into their chromosomes.

Recombinant *Synechococcus* PCC7942 strains were constructed with Hyn's genes integrated into their chromosomes as shown in FIG. 13. The procedures for construct these recombinant strains are listed below. First, we constructed in *E. coli* all the IPTG-inducible expression vectors that contain the structural and accessory genes of the hydrogenase Hyn in a cassette, such as SpecR/lacIq/PromterTrc/hynS/hynL, Spec$^R$/lacIq/PromterTrc/hynS/hynL/hynD, or Spec$^R$/lacIq/PromterTrc/hynS/hynL/hynD/hupK/hypC1/hypC2 (Spec$^R$ is an antibiotics selection marker). Second, we mixed the DNAs of these expression vectors separately with cyanobacterium *Synechococcus* PCC7942 that is naturally competent to foreign DNAs. Various expression cassettes then were integrated into the NS I site of the genome of *Synechococcus* PCC7942 through-homologous recombination, and recombinant strains were selected on spectinomycin plates. The accuracy of all the recombinant strains were confirmed by PCR, and Southern blotting. IPTG-inducible gene expression was confirmed by Western blotting.

Figure 14:
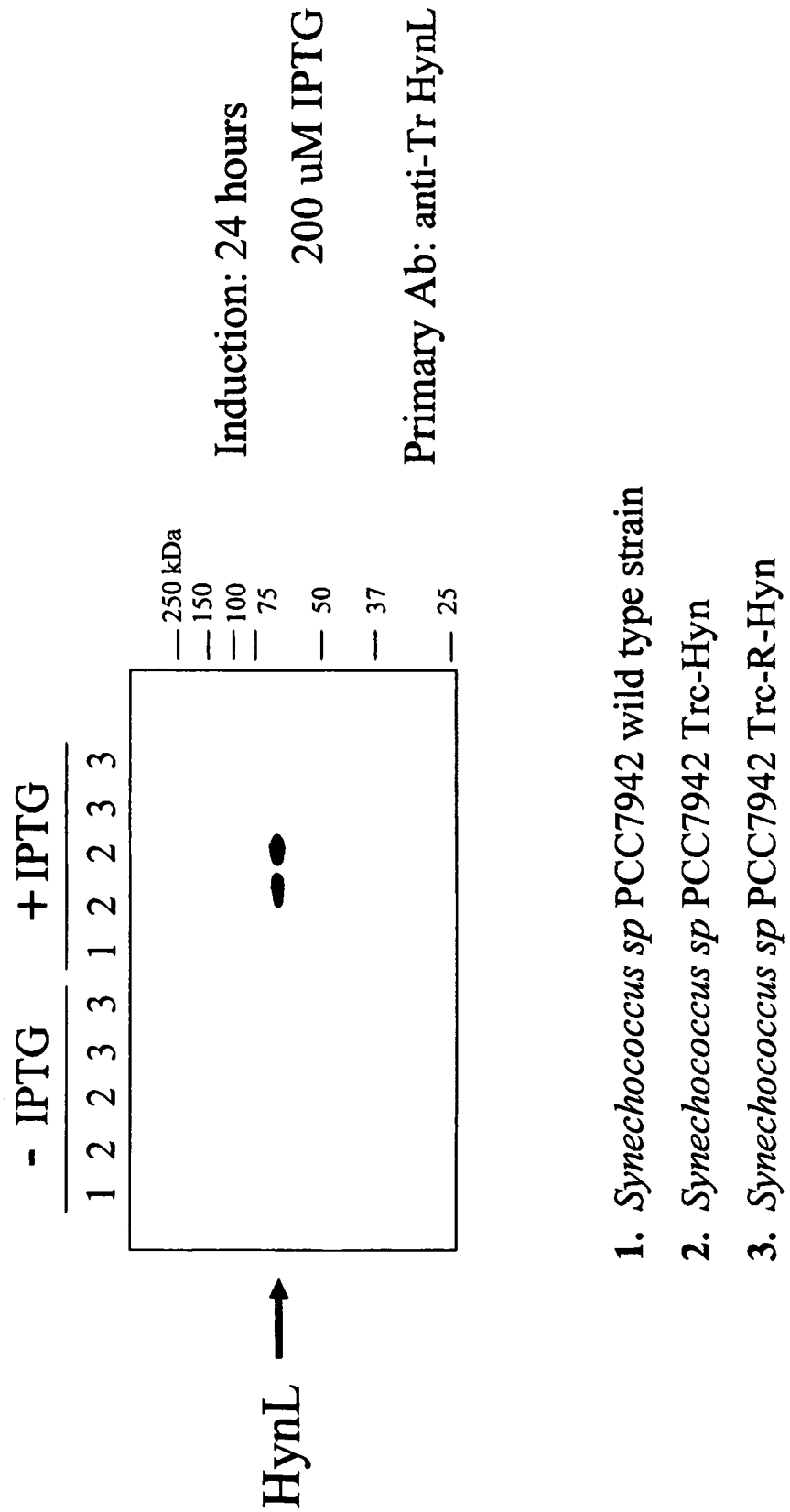
FIG. 14. IPTG-inducible expression of HynL in cyanobacterium *Synechococcus* sp PCC7942.
Figure 15:
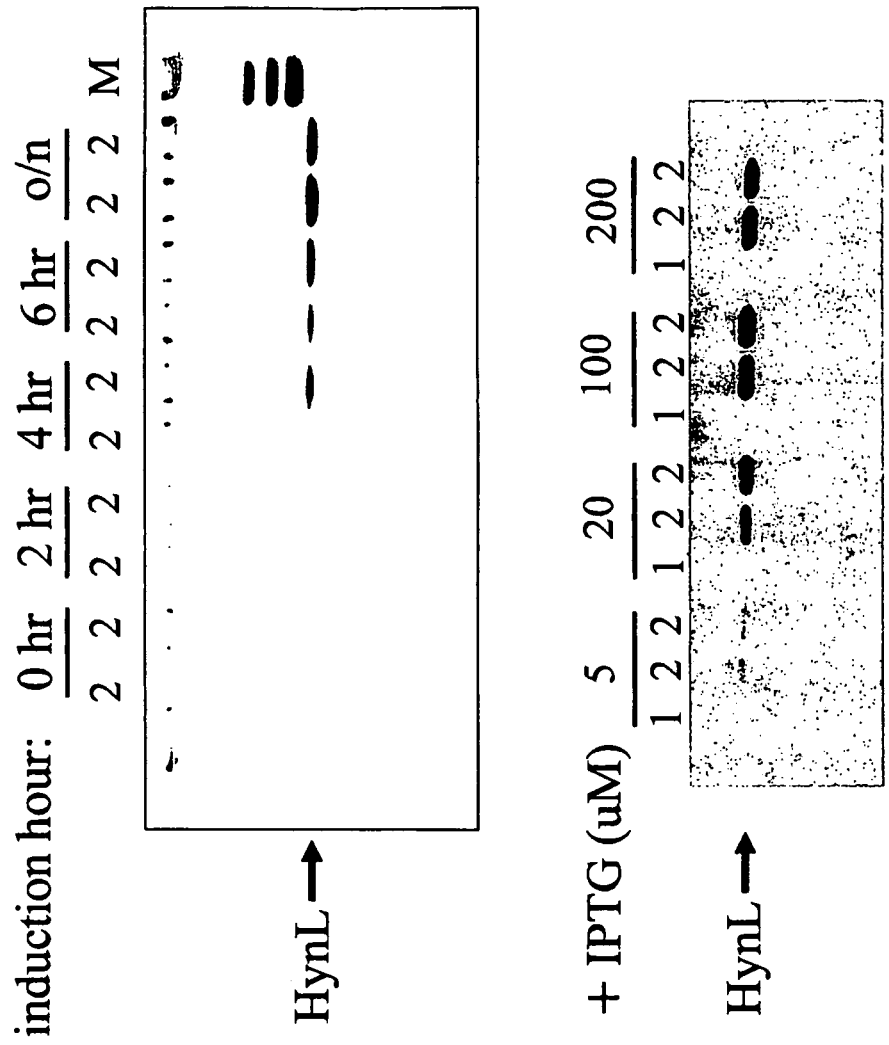
FIG. 15. Optimizing conditions of IPTG-inducible expression of Hyn in cyanobacterium *Synechococcus* sp PCC7942.
Figure 16:
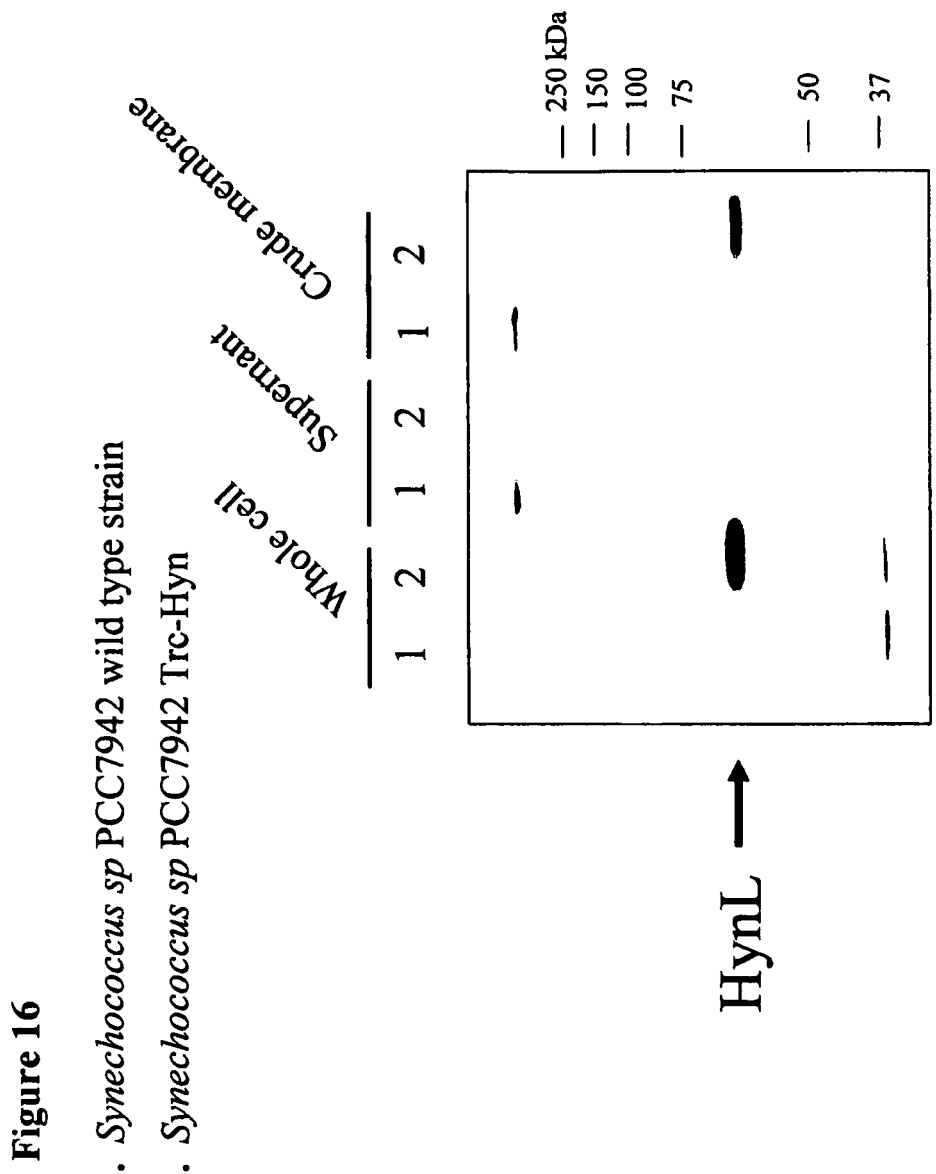
FIG. 16. Location of hetero-expressed Hyn in cyanobacterium *Synechococcus* sp PCC7942.

As demonstrated by Western blotting (FIG. 14), the $O_2$-tolerant hydrogenase Hyn is heterologously expressed in the recombinant cyanobacterium *Synechococcus* sp PCC7942 upon IPTG induction. Optimizing conditions of IPTG-inducible expression of Hyn in cyanobacterium *Synechococcus* sp PCC7942 are shown in FIG. 15. As shown in FIG. 16, *Synechococcus* sp PCC7942 was located in the membrane fraction.

All publications cited herein are hereby incorporated by reference.

While specific examples have been provided, the above description is illustrative and not restrictive. Any one or more of the features of the previously described embodiments can be combined in any manner with one or more features of any other embodiments in the present invention. Furthermore, many variations of the invention become apparent to those skilled in the art upon review of the specification. The scope of the invention should, therefore, be determined not with reference to the description herein, but instead should be determined with reference to the appended claims along with their full scope of equivalents.

We claim:

1. A recombinant cyanobacterium comprising:
an expressible recombinant nucleic acid which encodes a functional microbial oxygen-tolerant, hydrogen-evolving [NiFe]-hydrogenase that comprises a sequence at least 90% identical to the nucleic acid sequence from nucleotides 5091 to 6110 of SEQ ID NO: 5;

wherein the hydrogenase is present in an amount effective to produce a measurable amount of hydrogen when the recombinant cyanobacterium is incubated aerobically, in the presence of a suitable light source, with water as the feed stock.

2. The recombinant cyanobacterium of claim 1, wherein the suitable light source is solar energy or fluorescent light.

3. The recombinant cyanobacterium of one of claim 1, wherein the cyanobacterium is from the group of unicellular cyanobacteria.

4. The recombinant cyanobacterium of claim 1, wherein the recombinant cyanobacterium is *Synochocystis* or *Synechococcus*.

5. The recombinant cyanobacterium of claim 1, wherein the oxygen-tolerant, hydrogen-evolving [NiFe]-hydrogenase is derived from *Thiocapsa roseopersica*.

6. The recombinant cyanobacterium of claim 1, wherein the oxygen-tolerant, hydrogen-evolving [NiFe]-hydrogenase is derived from *Ralstonia eutropha* or *Alteromonas macleodii*.

7. The recombinant cyanobacterium of claim 1, wherein the oxygen-tolerant, hydrogen-evolving [NiFe]-hydrogenase is derived from a marine bacterium.

8. The recombinant cyanobacterium of claim 1 wherein the measurable amount of hydrogen is detected using gas chromatography.

9. The recombinant cyanobacterium of claim 1 wherein the measurable amount of hydrogen is detected using a Clark Electrode System.

10. An expression vector comprising a nucleic acid encoding a functional microbial oxygen-tolerant hydrogen-evolving [NiFe]-hydrogenase that comprises a sequence at least 90% identical to the nucleic acid sequence from nucleotides 5091 to 6110 of SEQ ID NO: 5.

11. A cyanobacterium which comprises the expression vector of claim 10.

12. A method for generating hydrogen from water, comprising culturing the recombinant cyanobacterium of claim 1 aerobically, under conditions effective to produce a measurable amount of hydrogen.

* * * * *